US006955875B2

(12) United States Patent
Rothenberg et al.

(10) Patent No.: US 6,955,875 B2
(45) Date of Patent: Oct. 18, 2005

(54) MUTATIONS ASSOCIATED WITH IRON DISORDERS

(75) Inventors: Barry E. Rothenberg, Delmar, CA (US); Ritsuko Sawada-Hirai, San Diego, CA (US); James C. Barton, Birmingham, AL (US)

(73) Assignee: Billups-Rothenberg, Inc., San Diego, CA (US)

( * ) Notice: Subject to any disclaimer, the term of this patent is extended or adjusted under 35 U.S.C. 154(b) by 0 days.

(21) Appl. No.: 09/981,606

(22) Filed: Oct. 16, 2001

(65) Prior Publication Data

US 2003/0129595 A1 Jul. 10, 2003

Related U.S. Application Data

(63) Continuation of application No. 09/277,457, filed on Mar. 26, 1999, now Pat. No. 6,355,425.

(51) Int. Cl.$^7$ .............................. C12Q 1/68; C12P 19/34; C07H 21/04

(52) U.S. Cl. .................... 435/6; 435/91.2; 536/23.1; 536/24.3; 536/24.31; 536/24.33

(58) Field of Search ................... 435/6, 91.2; 536/23.1, 536/24.3, 24.33, 22.1, 24.31, 24.32

(56) References Cited

U.S. PATENT DOCUMENTS

| | | | |
|---|---|---|---|
| 4,946,778 A | 8/1990 | Ladner et al. | 435/69.6 |
| 5,705,343 A | 1/1998 | Drayna et al. | 435/6 |
| 5,712,098 A | 1/1998 | Tsuchihashi et al. | 435/6 |
| 5,753,438 A | 5/1998 | Drayna et al. | 435/6 |
| 5,877,015 A | 3/1999 | Hardy et al. | 435/325 |
| 5,879,892 A | 3/1999 | Van Baren et al. | 435/6 |
| 5,879,904 A | 3/1999 | Brechot et al. | 435/69.1 |
| 5,879,908 A | 3/1999 | Laping et al. | 435/69.1 |
| 6,025,130 A | 2/2000 | Thomas et al. | 435/6 |
| 6,140,305 A | 10/2000 | Thomas et al. | 514/2 |
| 6,228,594 B1 | 5/2001 | Thomas et al. | 435/6 |
| 6,284,732 B1 | 9/2001 | Feder et al. | 514/13 |
| 6,355,425 B1 * | 3/2002 | Rothenberg et al. | 435/6 |

FOREIGN PATENT DOCUMENTS

WO    WO 98/14466    4/1998

OTHER PUBLICATIONS

Barton, et al., Two Novel Missence Mutations of the HFE Gene (I105T and G93R) and Identification of the S65C Mutation in Alabama Hemochromatosis Probands, Blood Cells, Molecules, and Diseases, vol. 25, No. 9, 1999. pp. 147–155.

Bernard et al., Homogenous Multiplex Genotyping of Hemochromatosis Mutations with Fluorescent Hybridization Probes, Am. J. Pathology, vol. 153, No. 4, Oct., 1998. pp. 1055–1061.

Cheng et al., Preparation and hybridization analysis of DNA/RNA from *E. coli* on micro fabricated bioelectric chips, Nature biotechnology, vol. 16, pp. 541–546, Jun. 1998.

Edman et al., Electric field directed nucleic acid hybridization on microchips, Nucleic Acids Research, 1997, vol. 25, No. 24, pp. 4907–4914.

Feder et al., "the Hemochromatosis Founder Mutation in HLA–H Disrupts . . . ", Journal of Biological chemistry vol. 272, No. 22, pp. 14025–14028, 1997.

Mura et al., HFE Mutations Analysis in 711 Hemochromatosis Probands: Evidence for S65C Implication in Mild Form of Hemochromatosis; BLOOD, vol. 93, No. 8, 19999, pp. 2502–2505.

Nikiforov et al., Genetic Bit Analysis : a solid phase method for typing single nucleotide polymorphisms Nucleic Acids Research, 1994, vol. 22, No. 2, 4167–4175.

Sanchez et al., Prevalence of the Cys282Tyr and His63Asp HFE gene mutations in Spanish patients with hereditary hemochromatosis and in controls; Journal of Hepatology 1998; pp. 725–728.

Sosnowski et al., Rapids determination of single base mismatch mutations in DNA hybrids by direct electric field control, Proc. Natl. Acad. Sci. USA, vol. 94, pp. 1119–1123, Feb. 1997.

Wenz et al., A rapid automated SSCP multiplex capillary electrophoreses protocol that detects the two common mutations implicated in hereditary hemochromastosis (HH); Hum. Genet., vol. 104, No. 1, 1999, pp. 29–35.

Beutler et al., "HLA–H and Associated Proteins in Patients with Hemochromatosis" Mol. Med., vol. 3, No. 6, pp. 397–402, Jun. 1997.

Bjorkman et al., "The foreign antigen binding site and T cell recognition regions of class I histocompatibility antigens", Nature vol. 329, Oct. 8, 1987.

Anges et al., "Strongly increased efficiency of altered peptide ligands by mannosylation" International Immunology, vol. 10, No. 9, pp. 1299–1304.

Bonkovsky et al., "Porphyria Cutanea Tarda, Hepatitis C, and HFE Gene Mutation sin North America", Hepatology Jun. 1998; vol. 27, No. 6, pp. 1661–1669.

Bulaj et al., Clinical and Biochemical Abnormalities in People Heterozygous for Hemochromatosis, N.E. Journal of Medicine, Dec. 1996, Vo.. 335, No. 24, pp. 1799–1805.

(Continued)

*Primary Examiner*—Cynthia Wilder
(74) *Attorney, Agent, or Firm*—Mintz Levin Cohn Ferris Glovsky & Popeo, PC; Ingrid A. Beattle; Janine M. Susan

(57) ABSTRACT

The invention features a method of diagnosing an iron disorder, e.g., hemochromatosis, or a genetic susceptibility to developing such a disorder in a mammal by determining the presence of a mutation in exon 2 or in an intron of an HFE nucleic acid.

11 Claims, 3 Drawing Sheets

OTHER PUBLICATIONS

Clevers et al., "Mutations of the hereditary hemochromatosis candidate gene HLA–H in porphyris cutanea tarda" N. Engl. Med May 1, 1997; 336(18):1327:8.

Douabin et al., "Ploymorphisms in the HFDE Gene" Hum. Hered. vol. 49, No. 1, pp. 21–26, Jan. 1999.

Fargion et al., "Genetic hemochromatosis in Italian patients with porphyria cutanea tarda", Journal of Hepatology 1996; 24:564–569.

Gerhard, Walter, "Fusion of Cells in Suspension and Outgrowth of Hybrids in Conditioned Medium", Plenum Press, Fusion Protocols, pp. 370–371, 1980.

Ghose et al., "Strategy for Linkage of Cytotoxic Agents", Methods in Ezzymology, vol. 93, 1983, pp. 281–333.

Kohler et al., "Continuous cultures of fusted cells secreting antibody of predefined specificity", Nature vol. 256, Aug. 7, 1975 pp. 495–497.

Lebron et al., "Crystal Structure of the Hemochromatosis Protein HFE and Characterization of Its Interaction with Transferring Receptor", vol. 93, 111–123, Apr. 3, 1998.

Lefkowitch, MD, "Iron–Rich Foci in Chronic Viral Hepatitis", Human Pathology, vol. 29, No. 2, Feb. 1998 pp., 116–118.

Mendez et al., "Familial porphyria Cutanea Tarda: Characterization of Seven Novel Uroporphyrinogen . . . ", Am. J. Hum. Genet. 63:1363–1375, 1998.

Nickerson et al., "Automated DNA diagnostic using an ELISA–based oligonucleotide ligation assay", Proc. Natl. Acad. Sci. USA, vol. 87, pp. 8923–8927, 1990.

O'Reilly et al., "Screening of Patients with Iron Overload to Identify Hemochromatosis and Porphyria utania Tarda", Arch Dermatol/vol. 133, Sep. 1997, pp. 1098–1101.

Roberts et al., "Increased frequency of the haemochromatosis Cys282Tur mutation in sporadic prophyria cutanea tarda", The Lancet 1997; 349:321–23.

Roberts et al., "The Frequency of Hemochromatosis–Associated Alleles is Increased in British Patients with Sporadic Porphyria Cutanea Tarda", Hepatology vol. 25, No. 1, 1997, pp. 159–161.

Rust et al., "Mutagenically separated PCR (MS–PCR): a highly specific one step procedure for easy mutation detection", Nucleic Acids Research, 1993, vol. 21, No. 6, 3623–3629.

Sampietro et al., "High Prevalence of the His63Asp HPE Mutation in Italian Patients with Porphyria Cutanea Tarda", Hepatology vol. 27, No. 1, 1998.

Stuart et al., "The C282Y mutation in the haemochromatosis gene (HFE) and hepatitis C virus infection are independent cofactors for porphyria . . . ",. Jour. Of Hepatology, 1998; 28: 404–409.

Worwood, Mark, "Revisiting various iron overload syndromes after the haemochromatosis gene discovery", Journal of Hepatology, 1998; 28: 26–27.

* cited by examiner

SEQUENCE LISTING

<160> NUMBER OF SEQ ID NOS: 30

<210> SEQ ID NO 1
<211> LENGTH: 2506
<212> TYPE: DNA
<213> ORGANISM: Homo sapiens

<400> SEQUENCE: 1

| | | | | | | |
|---|---|---|---|---|---|---|
| atgggcccgc | gagccaggcc | ggcgcttctc | ctcctgatgc | ttttgcagac | cgcggtcctg | 60 |
| cagggcgct | tgctgcgttc | acactctctg | cactacctct | tcatgggtgc | ctcagagcag | 120 |
| gaccttggtc | tttccttgtt | tgaagctttg | ggctacgtgg | atgaccagct | gttcgtgttc | 180 |
| tatgatcatg | agagtcgccg | tgtggagccc | cgaactccat | gggtttccag | tagaatttca | 240 |
| agccagatgt | ggctgcagct | gagtcagagt | ctgaaaggt | gggatcacat | gttcactgtt | 300 |
| gacttctgga | ctattatgga | aaatcacaac | cacagcaagg | agtcccacac | cctgcaggtc | 360 |
| atcctgggct | gtgaaatgca | agaagacaac | agtaccgagg | ctactggaa | gtacgggtat | 420 |
| gatgggcagg | accaccttga | attctgccct | gacacactgg | attggagagc | agcagaaccc | 480 |
| agggcctggc | ccaccaagct | ggagtgggaa | aggcacaaga | ttcgggccag | gcagaacagg | 540 |
| gcctacctgg | agagggactg | ccctgcacag | ctgcagcagt | tgctggagct | ggggagaggt | 600 |
| gttttggacc | aacaagtgcc | tccttttggtg | aaggtgacac | atcatgtgac | ctcttcagtg | 660 |
| accactctac | ggtgtcgggc | cttgaactac | tacccccaga | acatcaccat | gaagtggctg | 720 |
| aaggataagc | agccaatgga | tgccaaggag | ttcgaaccta | agacgtatt | gcccaatggg | 780 |
| gatgggacct | accagggctg | gataaccttg | gctgtacccc | tggggaaga | gcagagatat | 840 |
| acgtgccagg | tggagcaccc | aggcctggat | cagccctca | ttgtgatctg | ggagccctca | 900 |
| ccgtctggca | ccctagtcat | ggagtcatc | agtggaattg | ctgttttgt | cgtcatcttg | 960 |
| ttcattggaa | ttttgttcat | aatattaagg | aagaggcagg | gttcaagagg | agccatgggg | 1020 |
| cactacgtct | tagctgaacg | tgagtgacac | gcagcctgca | gactcactgt | gggaaggaga | 1080 |
| caaaactaga | gactcaaaga | gggagtgcat | ttatgagctc | ttcatgtttc | aggagagagt | 1140 |
| tgaacctaaa | catagaaatt | gcctgacgaa | ctccttgatt | ttagccttct | ctgttcattt | 1200 |
| cctcaaaaag | atttccccat | ttaggtttct | gagttcctgc | atgccggtga | tcctagctg | 1260 |
| tgacctctcc | cctggaactg | tctctcatga | acctcaagct | gcatctagag | gcttccttca | 1320 |
| tttcctccgt | cacctcagag | acatacacct | atgtcatttc | atttcctatt | tttggaagag | 1380 |
| gactccttaa | atttgggga | cttacatgat | tcattttaac | atctgagaaa | agctttgaac | 1440 |
| cctgggacgt | ggctagtcat | aaccttacca | gattttaca | catgtatcta | tgcatttct | 1500 |
| ggacccgttc | aactttttcct | ttgaatcctc | tctctgtgtt | acccagtaac | tcatctgtca | 1560 |
| ccaagccttg | gggattcttc | catctgattg | tgatgtgagt | tgcacagcta | tgaaggctgt | 1620 |
| gcactgcacg | aatggaagag | gcacctgtcc | cagaaaaagc | atcatggcta | tctgtgggta | 1680 |
| gtatgatggg | tgttttttagc | aggtaggagg | caaatatctt | gaaagggtt | gtgaagaggt | 1740 |
| gttttttcta | attggcatga | aggtgtcata | cagatttgca | agtttaatg | gtgccttcat | 1800 |
| ttgggatgct | actctagtat | tccagacctg | aagaatcaca | ataattttct | acctggtctc | 1860 |
| tccttgttct | gataatgaaa | attatgataa | ggatgataaa | agcacttact | tcgtgtccga | 1920 |
| ctcttctgag | cacctactta | catgcattac | tgcatgcact | tcttacaata | attctatgag | 1980 |
| ataggtacta | ttatccccat | ttctttttta | aatgaagaaa | gtgaagtagg | ccgggcacgg | 2040 |

-continued

```
tggctcgcgc ctgtggtccc agggtgctga gattgcaggt gtgagccacc ctgcccagcc      2100
gtcaaaagag tcttaatata tatatccaga tggcatgtgt ttactttatg ttactacatg      2160
cacttggctg cataaatgtg gtacaaccat tctgtcttga agggcaggtg cttcaggata      2220
ccatatacag ctcagaagtt tcttctttag gcattaaatt ttagcaaaga tatctcatct      2280
cttcttttaa accattttct tttttgtgg ttagaaaagt tatgtagaaa aaagtaaatg        2340
tgatttacgc tcattgtaga aaagctataa aatgaataca attaaagctg ttatttaatt      2400
agccagtgaa aaactattaa caacttgtct attacctgtt agtattattg ttgcattaaa      2460
aatgcatata ctttaataaa tgtacattgt attgtaaaaa aaaaaa                     2506
```

<210> SEQ ID NO 2
<211> LENGTH: 348
<212> TYPE: PRT
<213> ORGANISM: Homo sapiens

<400> SEQUENCE: 2

```
Met Gly Pro Arg Ala Arg Pro Ala Leu Leu Leu Met Leu Leu Gln
 1               5                  10                  15

Thr Ala Val Leu Gln Gly Arg Leu Leu Arg Ser His Ser Leu His Tyr
                20                  25                  30

Leu Phe Met Gly Ala Ser Glu Gln Asp Leu Gly Leu Ser Leu Phe Glu
            35                  40                  45

Ala Leu Gly Tyr Val Asp Asp Gln Leu Phe Val Phe Tyr Asp His Glu
        50                  55                  60

Ser Arg Arg Val Glu Pro Arg Thr Pro Trp Val Ser Ser Arg Ile Ser
65                  70                  75                  80

Ser Gln Met Trp Leu Gln Leu Ser Gln Ser Leu Lys Gly Trp Asp His
                85                  90                  95

Met Phe Thr Val Asp Phe Trp Thr Ile Met Glu Asn His Asn His Ser
            100                 105                 110

Lys Glu Ser His Thr Leu Gln Val Ile Leu Gly Cys Glu Met Gln Glu
        115                 120                 125

Asp Asn Ser Thr Glu Gly Tyr Trp Lys Tyr Gly Tyr Asp Gly Gln Asp
    130                 135                 140

His Leu Glu Phe Cys Pro Asp Thr Leu Asp Trp Arg Ala Ala Glu Pro
145                 150                 155                 160

Arg Ala Trp Pro Thr Lys Leu Glu Trp Glu Arg His Lys Ile Arg Ala
                165                 170                 175

Arg Gln Asn Arg Ala Tyr Leu Glu Arg Asp Cys Pro Ala Gln Leu Gln
            180                 185                 190

Gln Leu Leu Glu Leu Gly Arg Gly Val Leu Asp Gln Gln Val Pro Pro
        195                 200                 205

Leu Val Lys Val Thr His His Val Thr Ser Ser Val Thr Thr Leu Arg
    210                 215                 220

Cys Arg Ala Leu Asn Tyr Tyr Pro Gln Asn Ile Thr Met Lys Trp Leu
225                 230                 235                 240

Lys Asp Lys Gln Pro Met Asp Ala Lys Glu Phe Glu Pro Lys Asp Val
                245                 250                 255

Leu Pro Asn Gly Asp Gly Thr Tyr Gln Gly Trp Ile Thr Leu Ala Val
            260                 265                 270

Pro Pro Gly Glu Glu Gln Arg Tyr Thr Cys Gln Val Glu His Pro Gly
        275                 280                 285
```

```
Leu Asp Gln Pro Leu Ile Val Ile Trp Glu Pro Ser Pro Ser Gly Thr
    290                 295                 300

Leu Val Ile Gly Val Ile Ser Gly Ile Ala Val Phe Val Val Ile Leu
305                 310                 315                 320

Phe Ile Gly Ile Leu Phe Ile Ile Leu Arg Lys Arg Gln Gly Ser Arg
                325                 330                 335

Gly Ala Met Gly His Tyr Val Leu Ala Glu Arg Glu
            340                 345
```

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 3
cctcctacta cacatggtta agg                                          23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 4
gctctgacaa cctcaggaag g                                            21

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 5
ggtggaaata gggacctatt cc                                           22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 6
cactctgcca ctagactata gg                                           22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 7
gttccagtct tcctggcaag g                                            21

<210> SEQ ID NO 8

```
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 8
aaatgcttcc catggatgcc ag                                           22

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 9
aaaggatcca ccatgggccc gcgagccagg                                   30

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 10
gtgagtctgc aggctgcgtg                                              20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 11
gttccagtct tcctggcaag g                                            21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 12
aaatgcttcc catggatgcc ag                                           22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 13
gttccagtct tcctggcaag g                                            21

<210> SEQ ID NO 14
<211> LENGTH: 22
```

```
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 14
aaatgcttcc catggatgcc ag                                          22

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 15
gtgtggagcc tcaacatcct g                                           21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 16
acaagacctc agacttccag c                                           21

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 17
ggtggaaata gggacctatt cc                                          22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 18
cactctgcca ctagagtata gg                                          22

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 19
gttccagtct tcctggcaag g                                           21

<210> SEQ ID NO 20
<211> LENGTH: 21
<212> TYPE: DNA
```

```
<213> ORGANISM: Artificial Sequence
<220> FEATURE:
<223> OTHER INFORMATION: Description of Artificial Sequence:
      oligonucleotide primer

<400> SEQUENCE: 20
ttacctcctc aggcactcct c                                        21

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 21
aaaggatcca ccatgggccc gcgagccagg                               30

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 22
gtgagtctgc aggctgcgtg                                          20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 23
tgcctgagga ggtaattatg g                                        21

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 24
aaatgcttcc catggatgcc ag                                       22

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 25
tgcctgagga ggtaattatg g                                        21

<210> SEQ ID NO 26
<211> LENGTH: 22
<212> TYPE: DNA
<213> ORGANISM: Artificial Sequence
```

```
<220> FEATURE:
<223> OTHER INFORMATION: Description of Artificial Sequence:
      oligonucleotide primer

<400> SEQUENCE: 26
aaatgcttcc catggatgcc ag                                              22

<210> SEQ ID NO 27
<211> LENGTH: 12146
<212> TYPE: DNA
<213> ORGANISM: Homo sapiens

<400> SEQUENCE: 27
ggatccttta accgaggaga ttattatagc cggagctctg aagcagcaat ctcagttctt      60
gtgatagtga gcaaagaact acaaactaac accaaaatgc aagcttaaag caaagtttat     120
tgaagcacaa taatacactc tgagggacag cgggcttatt tctgcgaagt gaactcagca     180
cttctttaca gagctcaagg tgcttttatg gggtttgtgg ggaggagttg aggtttgggc     240
tgtatctgag tgacaggatg atgttatttg attgaagttt atagctatac aatctaaaat     300
taaactgtgc atggtcttac ctataatttg ttaagaaaag cctcccaggg atggggggc      360 aaaactgtat gtaaattcta ttataatgat ggcatgatga acttggggtg aacttgaaga     420
caggcttttg tgttgttggg catgtgccac cttagggaat ttccacctgt accctccttt     480
ctctttctcc aggatatttt ggccacagac tttatcataa actccatccc ttagggtggc     540
attagggtag tcttgggcct gaatttaggt gggccagtgg ctgtcttagt gacagccttt     600
ccgctctctt ctgtcatccc ctcccaactg ctaatgtcta actacctaac aattacccat     660
taaatcagtg tgtctgggt taggagcagg cctcaatatg tttaatcatt ctccagataa      720
tcccaatact gtaaagtttg tgaaacactt gtcagataat tcaattatga aggctgtgga     780
acgtgtttca gtaggatcta attggttaat gttatgactt aattaatttg aatcaaaaaa     840
caaaatgaaa aagctttata tttctaagtc aaataagaca taagttggtc taaggttgag     900
ataaaatttt taaatgtatg attgaatttt gaaaatcata aatatttaaa tatctaaagt     960
tcagatcaga acattgcgaa gctactttcc ccaatcaaca acacccctc aggatttaaa     1020 aaccaagggg gacactggat caccctagtgt tcacaagca ggtaccttct gctgtaggag     1080
agagagaact aaagttctga aagacctgtt gcttttcacc aggaagtttt actgggcatc     1140
tcctgagcct aggcaatagc tgtagggtga cttctggagc catccccgtt tcccgccc      1200 ccaaaagaag cggagattta acgggacgt gcggccagag ctggggaaat gggcccgcga      1260
gccaggccgg cgcttctcct cctgatgctt ttgcagaccg cggtcctgca ggggcgcttg     1320
ctgcgtgagt ccgagggctg cgggcgaact aggggcgcgg cggggtgga aaaatcgaaa      1380 ctagctttt ctttgcgctt gggagtttgc taactttgga ggacctgctc aacccaatcc      1440
gcaagcccct ctccctactt tctgcgtcca gaccccgtga gggagtgcct accactgaac     1500
tgcagatagg ggtccctcgc cccaggacct gcccctccc ccggctgtcc cggctctgcg      1560
gagtgacttt tggaaccgcc cactcccttc ccccaactag aatgcttta aataaatctc      1620 gtagttcctc acttgagctg agctaagcct ggggctcctt gaacctggaa ctcgggttta     1680
tttccaatgt cagctgtgca gttttttccc cagtcatctc caaacaggaa gttcttccct     1740
gagtgcttgc cgagaaggct gagcaaaccc acagcaggat ccgcacgggg tttccacctc     1800
agaacgaatg cgttgggcgg tggggcgcg aaagagtggc gttggggatc tgaattcttc      1860
accattccac ccacttttgg tgagacctgg ggtggaggtc tctagggtgg gaggctcctg     1920
```

```
agagaggcct acctcgggcc tttccccact cttggcaatt gttcttttgc ctggaaaatt    1980
aagtatatgt tagttttgaa cgtttgaact gaacaattct cttttcggct aggctttatt    2040
gatttgcaat gtgctgtgta attaagaggc ctctctacaa agtactgata atgaacatgt    2100
aagcaatgca ctcacttcta agttacattc atatctgatc ttatttgatt ttcactaggc    2160 ataggaggt aggagctaat aatacgttta ttttactaga agttaactgg aattcagatt    2220
atataactct tttcaggtta caaagaacat aaataatctg gttttctgat gttatttcaa    2280
gtactacagc tgcttctaat cttagttgac agtgattttg ccctgtagtg tagcacagtg    2340
ttctgtgggt cacacgccgg cctcagcaca gcactttgag ttttggtact acgtgtatcc    2400
acattttaca catgacaaga atgaggcatg cacggcctg cttcctggca aatttattca    2460
atggtacacg gggctttggt ggcagagctc atgtctccac ttcatagcta tgattcttaa    2520
acatcacact gcattagagg ttgaataata aaatttcatg ttgagcagaa atattcattg    2580
tttacaagtg taaatgagtc ccagccatgt gttgcactgt tcaagcccca agggagagag    2640
cagggaaaca agtctttacc ctttgatatt ttgcattcta gtgggagaga tgacaataag    2700
caaatgagca gaaagatata caacatcagg aaatcatggg tgttgtgaga agcagagaag    2760
tcagggcaag tcactctggg gctgacactt gagcagagac atgaaggaaa taagaatgat    2820
attgactggg agcagtattt cccaggcaaa ctgagtgggc ctggcaagtt ggattaaaaa    2880
gcgggttttc tcagcactac tcatgtgtgt gtgtgtgggg ggggggcgg cgtgggggtg    2940 ggaaggggga ctaccatctg catgtaggat gtctagcagt atcctgtcct ccctactcac    3000
taggtgctag gagcactccc ccagtcttga caaccaaaaa tgtctctaaa ctttgccaca    3060
tgtcacctag tagacaaact cctggttaag aagctcgggt tgaaaaaaat aaacaagtag    3120
tgctggggag tagaggccaa gaagtaggta atgggctcag aagaggagcc acaaacaagg    3180
ttgtgcaggc gcctgtaggc tgtggtgtga attctagcca aggagtaaca gtgatctgtc    3240
acaggctttt aaaagattgc tctggctgct atgtggaaag cagaatgaag ggagcaacag    3300
taaaagcagg gagcccagcc aggaagctgt tacacagtcc aggcaagagg tagtggagtg    3360
ggctgggtgg gaacagaaaa gggagtgaca aaccattgtc tcctgaatat attctgaagg    3420
aagttgctga aggattctat gttgtgtgag agaaagagaa gaattggctg ggtgtagtag    3480
ctcatgccaa ggaggaggcc aaggagagca gattcctgag ctcaggagtt caagaccagc    3540
ctgggcaaca cagcaaaacc ccttctctac aaaaaataca aaaattagct gggtgtggtg    3600
gcatgcacct gtgatcctag ctactcggga ggctgaggtg gagggtattg cttgagccca    3660
ggaagttgag gctgcagtga gccatgactg tgccactgta cttcagccta ggtgacagag    3720
caagaccctg tctcccctga cccctgaaa agagaagag ttaaagttga ctttgttctt    3780 tatttaatt ttattggcct gagcagtggg gtaattggca atgccatttc tgagatggtg    3840
aaggcagagg aaagagcagt ttggggtaaa tcaaggatct gcatttggac atgttaagtt    3900
tgagattcca gtcaggcttc caagtggtga ggccacatag gcagttcagt gtaagaattc    3960
aggaccaagg cagggcacgg tggctcactt ctgtaatccc agcactttgg tggctgaggc    4020
aggtagatca tttgaggtca ggagtttgag acaagcttgg ccaacatggt gaaaccccat    4080
gtctactaaa aatacaaaaa ttagcctggt gtggtggcgc acgcctatag tcccaggttt    4140
tcaggaggct taggtaggag aatcccttga acccaggagg tgcaggttgc agtgagctga    4200
gattgtgcca ctgcactcca gcctgggtga tagagtgaga ctctgtctca aaaaaaaaa    4260
```

```
aaaaaaaaaa aaaaaaaaaa aactgaagga attattcctc aggatttggg tctaatttgc    4320
cctgagcacc aactcctgag ttcaactacc atggctagac acaccttaac attttctaga    4380
atccaccagc tttagtggag tctgtctaat catgagtatt ggaataggat ctggggggcag   4440 tgagggggtg gcagccacgt gtggcagaga aaagcacaca aggaaagagc acccaggact    4500
gtcatatgga agaaagacag gactgcaact cacccttcac aaaatgagga ccagacacag    4560
ctgatggtat gagttgatgc aggtgtgtgg agcctcaaca tcctgctccc ctcctactac    4620
acatggttaa ggcctgttgc tctgtctcca ggttcacact ctctgcacta cctcttcatg    4680
ggtgcctcag gcaggacct  tggtcttttcc ttgtttgaag ctttgggcta cgtggatgac    4740
cagctgttcg tgttctatga tcatgagagt cgccgtgtgg agccccgaac tccatgggtt    4800
tccagtagaa tttcaagcca gatgtggctg cagctgagtc agagtctgaa agggtgggat    4860
cacatgttca ctgttgactt ctggactatt atggaaaatc acaaccacag caagggtatg    4920
tggagagggg gcctcacctt cctgaggttg tcagagcttt tcatcttttc atgcatcttg    4980
aaggaaacag ctggaagtct gaggtcttgt gggagcaggg aagagggaag gaatttgctt    5040
cctgagatca tttggtcctt ggggatggtg gaaatagggg cctattcctt tggttgcagt    5100
taacaaggct ggggattttt ccagagtccc acaccctgca ggtcatcctg ggctgtgaaa    5160
tgcaagaaga caacagtacc gagggctact ggaagtacgg gtatgatggg caggaccacc    5220
ttgaattctg ccctgacaca ctggattgga gagcagcaga acccagggcc tggcccacca    5280
agctggagtg ggaaaggcac aagattcggg ccaggcagaa cagggcctac ctggagaggg    5340
actgccctgc acagctgcag cagttgctgg agctggggag aggtgttttg gaccaacaag    5400
gtatggtgga aacacacttc tgcccctata ctctagtggc agagtggagg aggttgcagg    5460
gcacggaatc cctggttgga gtttcagagg tggctgaggc tgtgtgcctc tccaaattct    5520
gggaagggac tttctcaatc ctagagtctc taccttataa ttgagatgta tgagacagcc    5580
acaagtcatg ggtttaattt cttttctcca tgcatatggc tcaaagggaa gtgtctatgg    5640
cccttgcttt ttatttaacc aataatcttt tgtatattta tacctgttaa aaattcagaa    5700
atgtcaaggc cgggcacggt ggctcacccc tgtaatccca gcactttggg aggccgaggc    5760
gggtggtcac aaggtcagga gtttgagacc agcctgacca catggtgaaa acccgtctct    5820
aaaaaaatac aaaaattagc tggtcacagt catgcgcacc tgtagtccca gctaattgga    5880
aggctgaggc aggagcatcg cttgaacctg ggaagcggaa gttgcactga gccaagatcg    5940
cgccactgca ctccagccta ggcagcagag tgagactcca tcttaaaaaa aaaaaaaaaa    6000
aaaaagagaa ttcagagatc tcagctatca tatgaatacc aggacaaaat atcaagtgag    6060
gccacttatc agagtagaag aatcctttag gttaaaagtt tctttcatag aacatagcaa    6120
taatcactga agctacctat cttacaagtc cgcttcttat aacaatgcct cctaggttga    6180
cccaggtgaa actgaccatc tgtattcaat cattttcaat gcacataaag ggcaatttta    6240
tctatcagaa caaagaacat gggtaacaga tatgtatatt tacatgtgag gagaacaagc    6300
tgatctgact gctctccaag tgacactgtg ttagagtcca atcttaggac acaaaatggt    6360
gtctctcctg tagcttgttt ttttctgaaa agggtatttc cttcctccaa cctatagaag    6420
gaagtgaaag ttccagtctt cctggcaagg gtaaacagat cccctctcct catccttcct    6480
ctttcctgtc aagtgcctcc tttggtgaag gtgacacatc atgtgacctc ttcagtgacc    6540
actctacggt gtcgggcctt gaactactac ccccagaaca tcaccatgaa gtggctgaag    6600
gataagcagc caatggatgc caaggagttc gaacctaaag acgtattgcc caatggggat    6660
```

```
gggacctacc agggctggat aaccttggct gtaccccctg gggaagagca gagatatacg   6720
tgccaggtgg agcacccagg cctggatcag cccctcattg tgatctgggg tatgtgactg   6780
atgagagcca ggagctgaga aaatctattg ggggttgaga ggagtgcctg aggaggtaat   6840
tatggcagtg agatgaggat ctgctctttg ttaggggatg ggctgagggt ggcaatcaaa   6900
ggctttaact tgcttttttct gttttagagc cctcaccgtc tggcacccta gtcattggag   6960
tcatcagtgg aattgctgtt tttgtcgtca tcttgttcat tggaattttg ttcataatat   7020
taaggaagag gcagggttca agtgagtagg aacaagggg aagtctctta gtacctctgc   7080
cccagggcac agtgggaaga ggggcagagg ggatctggca tccatgggaa gcattttttct   7140 catttatatt ctttggggac accagcagct ccctgggaga cagaaaataa tggttctccc   7200
cagaatgaaa gtctctaatt caacaaacat cttcagagca cctactattt tgcaagagct   7260
gtttaaggta gtacagggggc tttgaggttg agaagtcact gtggctattc tcagaaccca   7320
aatctggtag ggaatgaaat tgatagcaag taaatgtagt taaagaagac cccatgaggt   7380
cctaaagcag gcaggaagca aatgcttagg gtgtcaaagg aaagaatgat cacattcagc   7440
tggggatcaa gatagccttc tggatcttga aggagaagct ggattccatt aggtgaggtt   7500
gaagatgatg ggaggtctac acagacggag caaccatgcc aagtaggaga gtataaggca   7560
tactgggaga ttagaaataa ttactgtacc ttaaccctga gtttgcttag ctatcactca   7620
ccaattatgc atttctaccc cctgaacatc tgtggtgtag ggaaagagaa atcagaaaga   7680
agccagctca tacagagtcc aagggtcttt tgggatattg ggttatgatc actgggtgt    7740 cattgaagga tcctaagaaa ggaggaccac gatctccctt atatggtgaa tgtgttgtta   7800
agaagttaga tgagaggtga ggagaccagt tagaaagcca ataagcattt ccagatgaga   7860
gataatggtt cttgaaatcc aatagtgccc aggtctaaat tgagatgggt gaatgaggaa   7920
aataaggaag agaagagg caagatggtg cctaggtttg tgatgcctct ttcctgggtc      7980
tcttgtctcc acaggaggag ccatggggca ctacgtctta gctgaacgtg agtgacacgc   8040
agcctgcaga ctcactgtgg gaaggagaca aaactagaga ctcaaagagg gagtgcattt    8100
atgagctctt catgtttcag gagagagttg aacctaaaca tagaaattgc ctgacgaact   8160
ccttgatttt agccttctct gttcatttcc tcaaaaagat ttccccattt aggtttctga   8220
gttcctgcat gccggtgatc cctagctgtg acctctcccc tggaactgtc tctcatgaac   8280
ctcaagctgc atctagaggc ttccttcatt tcctccgtca cctcagagac atacacctat   8340
gtcatttcat ttcctatttt tggaagagga ctccttaaat ttgggggact tacatgattc   8400
attttaacat ctgagaaaag ctttgaaccc tgggacgtgg ctagtcataa ccttaccaga   8460
tttttacaca tgtatctatg catttctgg acccgttcaa cttttccttt gaatcctctc     8520
tctgtgttac ccagtaactc atctgtcacc aagccttggg gattcttcca tctgattgtg   8580
atgtgagttg cacagctatg aaggctgtac actgcacgaa tggaagaggc acctgtccca   8640
gaaaaagcat catggctatc tgtgggtagt atgatgggtg ttttttagcag gtaggaggca   8700 aatatcttga aaggggttgt gaagaggtgt tttttctaat tggcatgaag gtgtcataca   8760
gatttgcaaa gtttaatggt gccttcattt gggatgctac tctagtattc cagacctgaa   8820
gaatcacaat aattttctac ctggtctctc cttgttctga taatgaaaat tatgataagg   8880
atgataaaag cacttacttc gtgtccgact cttctgagca cctacttaca tgcattactg   8940
catgcacttc ttacaataat tctatgagat aggtactatt atccccattt ctttttttaaa   9000
```

```
tgaagaaagt gaagtaggcc gggcacggtg gctcacgcct gtaatcccag cactttggga      9060
ggccaaagcg ggtggatcac gaggtcagga gatcgagacc atcctggcta acatggtgaa      9120
accccatctc taataaaaat acaaaaaatt agctgggcgt ggtggcagac gcctgtagtc      9180
ccagctactc ggaaggctga ggcaggagaa tggcatgaac caggaggca gagcttgcag        9240
tgagccgagt ttgcgccact gcactccagc ctaggtgaca gagtgagact ccatctcaaa      9300
aaaataaaaa taaaataaaa aaaatgaaaa aaaaagaaaa gtgaagtata gagtatctca      9360
tagtttgtca gtgatagaaa caggtttcaa actcagtcaa tctgaccgtt tgatacatct      9420
cagacaccac tacattcagt agtttagatg cctagaataa atagagaagg aaggagatgg      9480
ctcttctctt gtctcattgt gttcttctg aatgagcttg aatcacatga aggggaacag       9540
cagaaaacaa ccaactgatc ctcagctgtc atgtttcctt aaaagtccc tgaaggaagg       9600
tcctggaatg tgactcccctt gctcctctgt tgctctcttt ggcattcatt tctttggacc    9660
ctacgcaagg actgtaattg gtggggacag ctagtggccc tgctgggctt cacacacggt      9720
gtcctcccta ggccagtgcc tctggagtca gaactctggt ggtatttccc tcaatgaagt      9780
ggagtaagct ctctcatttt gagatggtat aatggaagcc accaagtggc ttagaggatg      9840
cccaggtcct tccatggagc cactgggggtt ccggtgcaca ttaaaaaaaa aatctaacca    9900
ggacattcag gaattgctag attctgggaa atcagttcac catgttcaaa agagtctttt      9960
tttttttttt gagactctat tgcccaggct ggagtgcaat ggcatgatct cggctcactg     10020
taacctctgc ctcccaggtt caagcgattc tcctgtctca gcctcccaag tagctgggat     10080
tacaggcgtg caccaccatg cccggctaat ttttgtattt ttagtagaga cagggtttca     10140
ccatgttggc caggctggtc tcgaactctc ctgacctcgt gatccgcctg cctcggcctc     10200
ccaaagtgct gagattacag gtgtgagcca ccctgcccag ccgtcaaaag agtcttaata     10260
tatatatcca gatggcatgt gtttacttta tgttactaca tgcacttggc tgcataaatg     10320
tggtacaagc attctgtctt gaagggcagg tgcttcagga taccatatac agctcagaag     10380
tttcttcttt aggcattaaa ttttagcaaa gatatctcat ctcttctttt aaaccattt      10440
cttttttttgt ggttagaaaa gttatgtaga aaaagtaaa tgtgatttac gctcattgta     10500
gaaaagctat aaaatgaata caattaaagc tgttattta ttagccagtg aaaaactatt     10560
aacaacttgt ctattacctg ttagtattat tgttgcatta aaaatgcata actttaata     10620
aatgtacatt gtattgtata ctgcatgatt ttattgaagt tcttgttcat cttgtgtata     10680
tacttaatcg ctttgtcatt ttggagacat ttattttgct tctaattct ttacatttg       10740
tcttacggaa tattttcatt caactgtggt agccgaatta atcgtgtttc ttcactctag     10800
ggacattgtc gtctaagttg taagacattg gttatttac cagcaaacca ttctgaaagc     10860
atatgacaaa ttatttctct cttaatatct tactatactg aaagcagact gctataaggc     10920
ttcacttact cttctacctc ataaggaata tgttacaatt aatttattag gtaagcattt     10980
gttttatatt ggttttattt cacctgggct gagatttcaa gaaacacccc agtcttcaca     11040
gtaacacatt tcactaacac atttactaaa catcagcaac tgtggcctgt taatttttt    11100
aatagaaatt ttaagtcctc attttctttc ggtgttttt aagcttaatt tttctggctt      11160
tattcataaa ttcttaaggt caactacatt tgaaaaatca aagacctgca ttttaaattc     11220
ttattcacct ctggcaaaac cattcacaaa ccatggtagt aaagagaagg gtgacacctg     11280
gtggccatag gtaaatgtac cacggtggtc cggtgaccag agatgcagcg ctgagggttt     11340
tcctgaaggt aaaggaataa agaatggtg gaggggcgtg cactggaaat cacttgtaga      11400
```

```
gaaaagccccc tgaaaatttg agaaaacaaa caagaaacta cttaccagct atttgaattg    11460
ctggaatcac aggccattgc tgagctgcct gaactgggaa cacaacagaa ggaaaacaaa    11520
ccactctgat aatcattgag tcaagtacag caggtgattg aggactgctg agaggtacag    11580
gccaaaattc ttatgttgta ttataataat gtcatcttat aatactgtca gtattttata    11640
aaacattctt cacaaactca cacacattta aaaacaaaac actgtctcta aaatccccaa    11700 attttcata aactcagttt taaactaact tttttcaaa ccacaatctg atttaacaat       11760
gactatcatt taaatatttc tgactttcaa attaaagatt ttcacatgca ggctgatatt    11820
tgtaattgtg attctctctg taggctttgg gtataatgtg ttcttttcct tttttgcatc    11880
agcgattaac ttctacactc taacatgtag aatgttacta caatattaaa gtattttgta    11940
tgacaatttt atttgaaagc ctaggatgcg ttgacatcct gcatgcattt attacttgat    12000
atgcatgcat tctggtatct caagcattct atttctgagt aattgtttaa ggtgtagaag    12060
agatagatat ggtggatttg gagttgatac ttatatattt tctatttctt ggatggatga    12120
atttgtacat taaaagttttt ccatgg                                         12146
```

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 28
gtctgaaacg gtgggat                                                    17

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 29
acttctggac tactatgg                                                   18

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 30
atcatgagtg tcgccgt                                                    17

MUTATIONS ASSOCIATED WITH IRON DISORDERS

RELATED APPLICATIONS

This application is a continuation of U.S. Ser. No. 09/277,457, filed Mar. 26, 1999 (now U.S. Pat. No. 6,355,425), the entire contents of which is hereby incorporated by reference.

BACKGROUND OF THE INVENTION

Hemochromatosis is the most common progressive (and sometimes fatal) genetic disease in people of European descent. Hemochromatosis is a disease state characterized by an inappropriate increase in intestinal iron absorption. The increase can result in deposition of iron in organs such as the liver, pancreas, heart, and pituitary. Such iron deposition can lead to tissue damage and functional impairment of the organs.

In some populations, 60–100% of cases are attributable to homozygosity for a missense mutation at C282Y in the Histocompatibility iron (Fe) loading (HFE) gene, a major histocompatibility (MHC) non-classical class I gene located on chromosome 6p. Some patients are compound heterozygotes for C282Y and another mutation at H63D.

SUMMARY OF THE INVENTION

The invention is based on the discovery of novel mutations which are associated with aberrant iron metabolims, absorption, or storage, or in advanced cases, clinical hemochromatosis. Accordingly, the invention features a method of diagnosing an iron disorder, e.g., hemochromatosis or a genetic susceptibility to developing such a disorder, in a mammal by determining the presence of a mutation in exon 2 of an HFE nucleic acid. The mutation is not a C→G missense mutation at position 187 of SEQ ID NO:1 which leads to a H63D substitution. The nucleic acid is an RNA or DNA molecule in a biological sample taken from the mammal, e.g. a human patient, to be tested. The presence of the mutation is indicative of the disorder or a genetic susceptibility to developing it. An iron disorder is characterized by an aberrant serum iron level, ferritin level, or percent saturation of transferrin compared to the level associated with a normal control individual. An iron overload disorder is characterized by abnormally high iron absorption compared to a normal control individual. Clinical hemochromatosis is defined by an elevated fasting transferrin saturation level of greater than 45% saturation.

For example, the mutation is a missense mutation at nucleotide 314 of SEQ ID NO:1 such as 314C which leads to the expression of mutant HFE gene product with amino acid substitution I105T. The I105T mutation is located in the α1 helix of the HFE protein and participates in a hydrophobic pocket (the "F" pocket). The alpha helix structure of the α1 domain spans residues S80 to N108, inclusive. The I105T mutation is associated with an iron overload disorder.

TABLE 1

Human HFE cDNA sequence (SEQ ID NO:1; GENBANK ® Accession No. U60319)

```
atgggcccg cgagccaggc cggcgcttct cctcctgatg cttttgcaga ccgcggtcct gcagggcgc ttgctgcgtt cacactctct gcactacctc ttcatgggtg cctcagagca ggaccttggt ctttccttgt ttgaagcttt gggctacgtg gatgaccagc tgttcgtgtt ctatgatcat gagagtcgcc
                                                        H63D     S65C gtgtggagcc ccgaactcca tgggtttcca gtagaatttc aagccagatg tggctgcagc tgagtcagag tctgaaaggg tgggatcaca tgttcactgt tgacttctgg actattatgg
                     G93R                                    I105T aaaatcacaa ccacagcaag gagtcccaca ccctgcaggt catcctgggc tgtgaaatgc aagaagacaa cagtaccgag ggctactgga agtacgggta tgatgggcag gaccaccttg aattctgccc tgacacactg gattggagag cagcagaacc cagggcctgg cccaccaagc tggagtggga aaggcacaag attcgggcca ggcagaacag ggcctacctg gagagggact gccctgcaca gctgcagcag ttgctggagc tggggagagg tgttttggac caacaagtgc ctcctttggt gaaggtgaca catcatgtga cctcttcagt gaccactcta cggtgtcggg ccttgaacta ctaccccag aacatcacca tgaagtggct gaaggataag cagccaatgg atgccaagga gttcgaacct aaagacgtat tgcccaatgg ggatgggacc taccagggct ggataacctt ggctgtaccc cctggggaag agcagagata tacgtgccag gtggagcacc caggcctgga tcagcccctc attgtgatct gggagccctc accgtctggc accctagtca ttggagtcat cagtggaatt gctgttttg tcgtcatctt gttcattgga attttgttca taatattaag gaagaggcag ggttcaagag gagccatggg gcactacgtc ttagctgaac gtgagtgaca cgcagcctgc agactcactg tgggaaggag acaaaactag agactcaaag
```

TABLE 1-continued

Human HFE cDNA sequence (SEQ ID NO:1; GENBANK ® Accession No. U60319)

```
agggagtgca tttatgagct cttcatgttt caggagagag ttgaacctaa acatagaaat
tgcctgacga actccttgat tttagccttc tctgttcatt tcctcaaaaa gatttcccca
tttaggtttc tgagttcctg catgccggtg atccctagct gtgacctctc ccctggaact
gtctctcatg aacctcaagc tgcatctaga ggcttccttc atttcctccg tcacctcaga
gacatacacc tatgtcattt catttcctat ttttggaaga ggactcctta aatttggggg
acttacatga ttcattttaa catctgagaa aagctttgaa ccctgggacg tggctagtca
taaccttacc agattttac acatgtatct atgcattttc tggacccgtt caacttttcc
tttgaatcct ctctctgtgt tacccagtaa ctcatctgtc accaagcctt ggggattctt
ccatctgatt gtgatgtgag ttgcacagct atgaaggctg tgcactgcac gaatggaaga
ggcacctgtc ccagaaaaag catcatggct atctgtgggt agtatgatgg gtgttttag
caggtaggag gcaaatatct tgaaaggggt tgtgaagagg tgttttttct aattggcatg
aaggtgtcat acagatttgc aaagtttaat ggtgccttca tttgggatgc tactctagta
ttccagacct gaagaatcac aataattttc tacctggtct ctccttgttc tgataatgaa
aattatgata aggatgataa aagcacttac ttcgtgtccg actcttctga gcacctactt
acatgcatta ctgcatgcac ttcttacaat aattctatga gataggtact attatcccca
tttctttttt aaatgaagaa agtgaagtag gccgggcacg gtggctcgcg cctgtggtcc
cagggtgctg agattgcagg tgtgagccac cctgcccagc cgtcaaaaga gtcttaatat
atatatccag atggcatgtg tttacttat gttactacat gcacttggct gcataaatgt
ggtacaacca ttctgtcttg aagggcaggt gcttcaggat accatataca gctcagaagt
ttcttcttta ggcattaaat tttagcaaag atatctcatc tcttcttta aaccattttc
ttttttttgtg gttagaaaag ttatgtagaa aaagtaaat gtgatttacg ctcattgtag
aaaagctata aaatgaatac aattaaagct gttatttaat tagccagtga aaaactatta
acaacttgtc tattacctgt tagtattatt gttgcattaa aaatgcatat actttaataa
atgtacattg tattgtaaaa aaaaaaa
```

TABLE 2

Human HFE gene product (SEQ ID NO:2; GENBANK ® Accession No. U60319)

MGPRARPALLLLMLLQTAVLQG

RLLRSHSLHYLFMGASEQDLGLSLFEALGYVDDQLFVFYDHESRRVEPRT

PWVSSRISSQMWLQLSOSLKGWDHMFTVDFWTIMENHNHSKESHTLQVIL

GCEMQEDNSTEGYWKYGYDGQDHLEFCPDTLDWRAAEPRAWPTKLEWERH

KIRARQNRAYLERDCPAQLQQLLELGRGVLDQQVPPLVKVTHHVTSSVTT

LRCRALNYYPQNITMKWLKDKQPMDAKEFEPKDVLPNGDGTYQGWITLAV

PPGEEQRYTCQVEHPGLDQPLIVIWEPSPSGTLVIGVISGIAVFVVILFI

GILFIILRKRQGSRGAMGHYVLAERE

Residues 1–22 =leader sequence; α1 domain underlined; residues 63, 65, 93, and 105 indicated in bold type)

Other mutations include nucleotide 277 of SEQ ID NO: 1, e.g., 277C which leads to expression of mutant HFE gene product G93R and one at nucleotide 193 of SEQ ID NO: 1, e.g., 193T, which leads to expression of mutant HFE gene product S65C.

Any biological sample containing an HFE nucleic acid or gene product is suitable for the diagnostic methods described herein. For example, the biological sample to be analyzed is whole blood, cord blood, serum, saliva, buccal tissue, plasma, effusions, ascites, urine, stool, semen, liver tissue, kidney tissue, cervical tissue, cells in amniotic fluid, cerebrospinal fluid, hair or tears. Prenatal testing can be done using methods used in the art, e.g., amniocentesis or chorionic villa sampling. Preferably, the biological sample is one that can be non-invasively obtained, e.g., cells in saliva or from hair follicles.

The assay is also used to screen individuals prior to donating blood to blood banks and to test organ tissue, e.g., a donor liver, prior to transplantation into a recipient patient. Both donors and recipients are screened.

In some cases, a nucleic acid is amplified prior to detecting a mutation. The nucleic acid is amplified using a first oligonucleotide primer which is 5' to exon 2 and a second oligonucleotide primer is 3' to exon 2. To detect mutation at nucleotide 314 of SEQ ID NO: 1, a first oligonucleotide primer which is 5' to nucleotide 314 and a second oligonucleotide primer which is 3' to nucleotide 314 is used in a standard amplification procedure such as polymerase chain reaction (PCR). To amplify a nucleic acid containing nucleotide 277 of SEQ ID NO: 1, a first oligonucleotide primer which is 5' to nucleotide 277 and a second oligonucleotide primer which is 3' to nucleotide 277 is used. Similarly, a nucleic acid containing nucleotide 193 of SEQ ID NO:1 is amplified using primers which flank that nucleotide. For example, for nucleotide 277, the first primer has a nucleotide sequence of SEQ ID NO: 3 and said second oligonucleotide primer has a nucleotide sequence of SEQ ID NO: 4, or the first primer has a nucleotide sequence of SEQ ID NO: 15 and said second oligonucleotide primer has a nucleotide sequence of SEQ ID NO: 16. Table 3, below, shows examples of primer pairs for amplification of nucleic acids in exons and introns of the HFE gene.

out to produce a mature RNA product, i.e., a mRNA, which is then transported to the cytoplasm. A method of diagnosing an iron disorder or a genetic susceptibility to developing the disorder is carried out by determining the presence or absence of a mutation in an intron of HFE genomic DNA in a biological sample. The presence of the mutation is indicative of the disorder or a genetic susceptibility to developing the disorder. The presence of a mutation in an intron is a marker for an exon mutation, e.g., a mutation in intron 4, e.g., at nucleotide 6884 of SEQ ID NO:27 is associated with the S65C mutation in exon 2. A mutation in intron 5, e.g., at nucleotide 7055 of SEQ ID NO:27 is associated with hemochromatosis. In some cases, intron mutations may adversely affect proper splicing of exons or may alter regulatory signals. Preferably, the intron 4 mutation is 6884C and the intron 5 mutation is 7055G. To amplify nucleic acid molecule containing nucleotide 6884 or 7055, primers which flank that nucleotide, e.g., those described in Table 3, are used according to standard methods. Nucleic acid-based diagnostic methods may or may not include a step of amplification to increase the number of copies of the nucleic acid to be analyzed. To detect a mutation in intron 4,

TABLE 3

| Target DNA | Forward Primer | Reverse Primer |
|---|---|---|
| | I. PRIMERS USED FOR AMPLIFICATION | |
| Exon 2 | CCTCCTACTACACATGGTTAAGG (SEQ ID NO: 3) | GCTCTGACAACCTCAGGAAGG (SEQ ID NO: 4) |
| Exon 3 | GGTGGAAATAGGGACCTATTCC (SEQ ID NO: 5) | CACTCTGCCACTAGACTATAGG (SEQ ID NO: 6) |
| Exon 4 | GTTCCAGTCTTCCTGGCAAGG (SEQ ID NO: 7) | AAATGCTTCCCATGGATGCCAG (SEQ ID NO: 8) |
| RT-PCR | AAAGGATCCACCATGGGCCCGCGAGCCAGG (SEQ ID NO: 9) | GTGAGTCTGCAGGCTGCGTG (SEQ ID NO: 10) |
| Intron 4 | GTTCCAGTCTTCCTGGCAAGG (SEQ ID NO: 11) | AAATGCTTCCCATGGATGCCAG (SEQ ID NO: 12) |
| Intron 5 | GTTCCAGTCTTCCTGGCAAGG (SEQ ID NO: 13) | AAATGCTTCCCATGGATGCCAG (SEQ ID NO: 14) |
| | II. PRIMERS USED FOR AMPLIFICATION | |
| Exon 2 | GTGTGGAGCCTCAACATCCTG (SEQ ID NO: 15) | ACAAGACCTCAGACTTCCAGC (SEQ ID NO: 16) |
| Exon 3 | GGTGGAAATAGGGACCTATTCC (SEQ ID NO: 17) | CACTCTGCCACTAGAGTATAGG (SEQ ID NO: 18) |
| Exon 4 | GTTCCAGTCTTCCTGGCAAGG (SEQ ID NO: 19) | TTACCTCCTCAGGCACTCCTC (SEQ ID NO: 20) |
| RT-PCR | AAAGGATCCACCATGGGCCCGCGAGCCAGG (SEQ ID NO: 21) | GTGAGTCTGCACGCTGCGTG (SEQ ID NO: 22) |
| Intron 4 | TGCCTGAGGAGGTAATTATGG (SEQ ID NO: 23) | AAATGCTTCCCATGGATGCCAG (SEQ ID NO: 24) |
| Intron 5 | TGCCTGAGGAGGTAATTATGG (SEQ ID NO: 25) | AAATGCTTCCCATGGATGCCAG (SEQ ID NO: 26) |

Mutations in introns of the HFE gene have now been associated with iron disorders and/or hemochromatosis. By "exon" is meant a segment of a gene the sequence of which is represented in a mature RNA product, and by "intron" is meant a segment of a gene the sequence of which is not represented in a mature RNA product. An intron is a part of a primary nuclear transcript which is subsequently spliced a patient-derived nucleic acid may be amplified using a first oligonucleotide primer which is 5' to intron 4 and a second oligonucleotide primer which is 3' to intron 4, and to detect a mutation in intron 5, the nucleic acid may be amplified using a first oligonucleotide primer which is 5' to intron 5 and a second oligonucleotide primer which is 3' to intron 5 (see, e.g., Table 3).

In addition to nucleic acid-based diagnostic methods, the invention includes a method of diagnosing an iron overload disorder or a genetic susceptibility thereto by determining the presence of a mutation in a HFE gene product in a biological sample. For example, the mutation results in a decrease in intramolecular salt bridge formation in the mutant HFE gene product compared to salt bridge formation in a wild type HFE gene product. The mutation which affects salt bridge formation is at or proximal to residue 63 of SEQ ID NO:2, but is not amino acid substitution H63D. Preferably, the mutation is between residues 23–113, inclusive of SEQ ID NO:2 (Table 2), more preferably, it is between residues 90–100, inclusive, of SEQ ID NO:2, more preferably, it is between residues 58–68, inclusive, of SEQ ID NO:2, and most preferably, the mutation is amino acid substitution S65C. Alternatively, the mutation which affects salt bridge formation is a mutation, e.g., an amino acid substitution at residue 95 or proximal to residue 95 of SEQ ID NO:2. Preferably, the mutation is G93R. Such an HFE mutation is detected by immunoassay or any other ligand binding assay such as binding of the HFE gene product to a transferrin receptor. Mutations are also detected by amino acid sequencing, analysis of the structural conformation of the protein, or by altered binding to a carbohydrate or peptide mimetope.

A mutation indicative of an iron disorder or a genetic susceptibility to developing such a disorder is located in the α1 helix (e.g., which spans residues 80–108, inclusive, of SEQ ID NO:2) of an HFE gene product. The mutation may be an addition, deletion, or substitution of an amino acid in the wild type sequence. For example, the mutant HFE gene product contains the amino acid substitution I105T or G93R or in the loop of the β sheet of the HFE molecule, e.g., mutation S65C Isolated nucleic acids encoding a mutated HFE gene products (and nucleic acids with nucleotide sequences complementary to such coding sequences) are also within the invention. Also included are nucleic acids which are at least 12 but less than 100 nucleotides in length. An isolated nucleic acid molecule is a nucleic acid molecule that is separated from the 5' and 3' sequences with which it is immediately contiguous in the naturally occurring genome of an organism. "Isolated" nucleic acid molecules include nucleic acid molecules which are not naturally occurring. For example, an isolated nucleic acid is one that has been amplified in vitro, e.g., by PCR; recombinantly produced; purified, e.g., by enzyme cleavage and gel separation; or chemically synthesized. For example, the restriction enzyme, Bst4C I (Sib Enzyme Limited, Novosibirsk, Russia), can be used to detect the G93R mutation (point mutation 277C); this enzyme cuts the mutated HFE nucleic acid but not the wild type HFE nucleic acid. Such nucleic acids are used as markers or probes for disease states. For example, a marker is a nucleic acid molecule containing a nucleotide polymorphism, e.g., a point mutation, associated with an iron disorder disease state flanked by wild type HFE sequences. The invention also encompasses nucleic acid molecules that hybridize, preferably under stringent conditions, to a nucleic acid molecule encoding a mutated HFE gene product (or a complementary strand of such a molecule). Preferably the hybridizing nucleic acid molecule is 400 nucleotides, more preferably 200 nucleotides, more preferably 100, more preferably 50, more preferably 25 nucleotides, more preferably 20 nucleotides, and most preferably 10–15 nucleotides, in length. For example, the nucleotide probe to detect a mutation is 13–15 nucleotides long. The nucleic acids are also used to produce recombinant peptides for generating antibodies specific for mutated HFE gene products. In preferred embodiments, an isolated nucleic acid molecule encodes an HFE polypeptide containing amino acid substitution I105T, G93R, or S65C, as well as nucleic acids the sequence of which are complementary to such nucleic acid which encode a mutant or wild type HFE gene product.

Also within the invention are substantially pure mutant HFE gene products, e.g., an HFE polypeptide containing amino acid substitution I105T, G93R, or S65C. Substantially pure or isolated HFE polypeptides include those that correspond to various functional domains of HFE or fragments thereof, e.g., a fragment of HFE that contains the α1 domain.

Wild type HFE binds to the transferrin receptor and regulates the affinity of transferrin receptor binding to transferrin. For example, a C282Y mutation in the HFE gene product reduces binding to the transferrin receptor, thus allowing the transferrin receptor to bind to transferrin (which leads to increased iron absorption).

The polypeptides of the invention encompass amino acid sequences that are substantially identical to the amino acid sequence shown in Table 2 (SEQ ID NO:2). Polypeptides of the invention are recombinantly produced, chemically synthesized, or purified from tissues in which they are naturally expressed according to standard biochemical methods of purification. Biologically active or functional polypeptides are those which possess one or more of the biological functions or activities of wild type HFE, e.g., binding to the transferrin receptor or regulation of binding of transferrin to the transferrin receptor. A functional polypeptide is also considered within the scope of the invention if it serves as an antigen for production of antibodies that specifically bind to an HFE epitope. In many cases, functional polypeptides retain one or more domains present in the naturally-occurring form of HFE.

The functional polypeptides may contain a primary amino acid sequence that has been altered from those disclosed herein. Preferably, the cysteine residues in exons 3 and 4 remain unchanged. Preferably the modifications consist of conservative amino acid substitutions. The terms "gene product", "protein", and "polypeptide" are used herein to describe any chain of amino acids, regardless of length or post-translational modification (for example, glycosylation or phosphorylation). Thus, the term "HFE polypeptide or gene product" includes full-length, naturally occurring HFE protein, as well a recombinantly or synthetically produced polypeptide that correspond to a full-length naturally occurring HFE or to a particular domain or portion of it.

The term "purified" as used herein refers to a nucleic acid or peptide that is substantially free of cellular material, viral material, or culture medium when produced by recombinant DNA techniques, or chemical precursors or other chemicals when chemically synthesized. Polypeptides are said to be "substantially pure" when they are within preparations that are at least 60% by weight (dry weight) the compound of interest. Preferably, the preparation is at least 75%, more preferably at least 90%, and most preferably at least 99%, by weight the compound of interest. Purity can be measured by any appropriate standard method, for example, by column chromatography, polyacrylamide gel electrophoresis, or HPLC analysis.

Diagnostic kits for identifying individuals suffering from or at risk of developing an iron disorder are also within the invention. A kit for detecting a nucleotide polymorphism associated with an iron disorder or a genetic susceptibility thereto contains an isolated nucleic acid which encodes at least a portion of the wild type or mutated HFE gene product, e.g., a portion which spans a mutation diagnostic for an iron disorder or hemochromatosis (or a nucleic acid the sequence of which is complementary to such a coding sequence). A kit for the detection of the presence of a mutation in exon 2 of an HFE nucleic acid contains a first oligonucleotide primer which is 5' to exon 2 and a second oligonucleotide primer is 3' to exon 2, and a kit for an antibody-based diagnostic assay includes an antibody which preferentially binds to an epitope of a mutant HFE gene product, e.g., an HFE polypeptide containing amino acid substitution I105T, G93R, or S65C, compared to its binding to the wild type HFE polypeptide. An increase in binding of the mutant HFE-specific antibody to a patient-derived sample (compared to the level of binding detected in a wild type sample or sample derived from a known normal control individual) indicates the presence of a mutation which is diagnostic of an iron disorder, i.e., that the patient from which the sample was taken has an iron disorder or is at risk of developing one. The kit may also contain an antibody which binds to an epitope of wild type HFE which contains residue 105, 93, or 65. In the latter case, reduced binding of the antibody to a patient-derived HFE gene product (compared to the binding to a wild type HFE gene product or a gene product derived from a normal control individual) indicates the presence of a mutation which is diagnostic of an iron disorder, i.e., that the patient from which the sample was taken has an iron disorder or is at risk of developing one.

Individual mutations and combinations of mutations in the HFE gene are associated with varying severity of iron disorders. For example, the C282Y mutation in exon 4 is typically associated with clinical hemochromatosis, whereas other HFE mutations or combinations of mutations in HFE nucleic acids are associated with disorders of varying prognosis. In some cases, hemochromatosis patients have been identified which do not have a C282Y mutation. The I105T and G93R mutations are each alone associated with an increased risk of iron overload (compared to, e.g., the H63D mutation alone), and the presence of both the I105T and H63D mutation is associated with hemochromatosis. Accordingly, the invention includes a method of determining the prognosis for hemochromatosis in a mammal suffering from or at risk of developing said hemochromatosis by (a) detecting the presence or absence of a first mutation in exon 4 in each allele of an HFE nucleic acid, e.g., patient-derived chromosomal DNA, and (b) detecting the presence of a second mutation in exon 2 in each allele of the nucleic acid. The presence of the first mutation in both chromosomes, i.e. an exon 4 homozygote such as a C282Y homozygote, indicates a more negative prognosis compared to the presence of the second mutation in one or both chromosomes, i.e., an exon 2 heterozygote or homozygote. An exon 4 mutation homozygote is also associated with a more negative prognosis compared to the presence of a first mutation (exon 4) in one allele and the presence of the second mutation (exon 2) in one allele, i.e., a compound heterozygote.

Other features and advantages of the invention will be apparent from the following detailed description, and from the claims.

DETAILED DESCRIPTION

Figure 1:
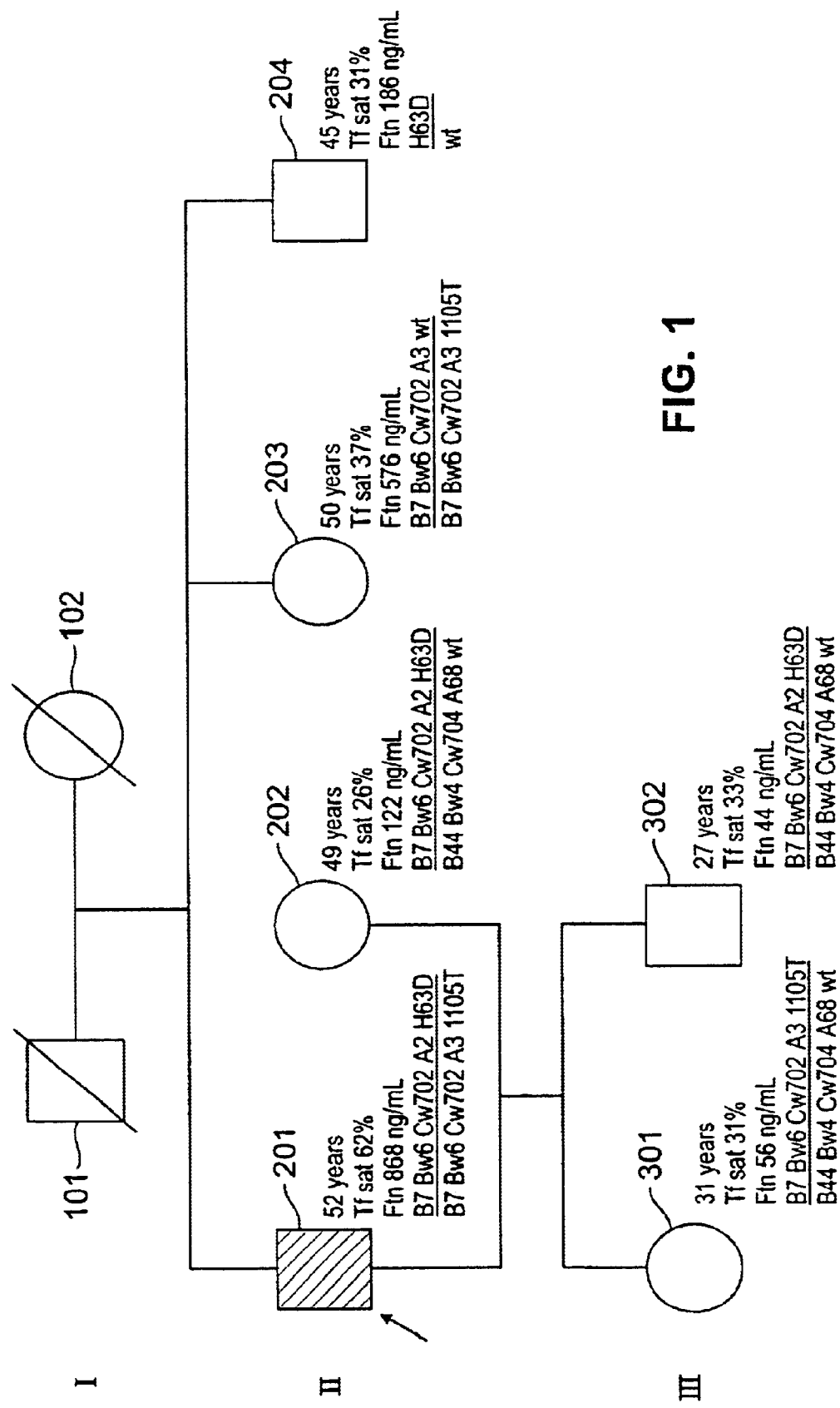
FIG. 1 is a diagram of the family of proband 1 (HFE genotype H63D/I105T). □=male, ●=female, ø=deceased, ■=hemochromatosis phenotype. Proband 1 is indicated by an arrow. Phenotype and genotype data: age in year saturation; % Ftn=serum ferritin concentration. I105 separate chromosomes. The sister of the proband (II, 203) has hyperferritinemia.

A proband is the first individual in a family identified to be affected by hemochromatosis. Forward and reverse sequencing of HFE exons 2, 3, 4, and 5, and of portions of HFE introns 2, 4, and 5 was carried out on biological samples taken from twenty hemochromatosis probands who lacked C282Y homozygosity, C282Y/H63D compound heterozygosity, or H63D homozygosity. Four probands had novel HFE coding region mutations. Probands 1 and 2 were heterozygous for previously undescribed mutations: exon 2, nt 314T→C (314C; I105T), and exon 2, nt 277G→C (277C; G93R), respectively; these probands were also heterozygous for H63D and C282Y, respectively. Probands 3 and 4 were heterozygous for an HFE mutation in exon 2, nt 193A→T (193T; S65C). Twelve other probands did not have an exon 2 HFE exon mutation; four were heterozygous for H63D. In probands 1, 2, 3, and 4, the amino acid substitutions I105T, G93R, and S65C (respectively) occurred on separate chromosomes from those with the C282Y or H63D mutations. In 176 normal control subjects, two were heterozygous for S65C; I105T and G93R were not detected in controls. Nine probands were heterozygous and two probands were homozygous for a base-pair change at intron 2, nt 4919T/C (SEQ ID NO:27). Heterozygosity for a base-pair change in intron 4 (nt 6884T→C) was detected only in probands 3 and 4, both of whom also had S65C and HLA-A32. The intron 2 mutation is not diagnostic of an iron disorder and appears randomly in the population. One proband was heterozygous for a base-pair change at intron 5 (nt 7055A→G).

The data described herein indicate that, in addition to the C282Y and H63D HFE mutations, the HFE exon and intron 5 mutations described herein are diagnostic (and prognostic) of iron disorders.

Pathology of Iron Overload

Iron plays an essential role in normal growth and development, but in elevated concentrations, iron is a toxic inorganic molecule and is the leading cause of death in children by poisoning. It has been implicated in the pathophysiology of a number of common diseases, e.g., hepatitis, cancer, heart disease, reperfusion injury, rheumatoid arthritis, diabetes, AIDS, and psychological abnormalities (e.g. depression).

The incidence of cancer (especially liver cancer) rises dramatically in the course of hemochromatosis. Iron, acting alone or in synergy with other environmental agents, catalyzes free radical formation. These free radicals which mediate tissue damage also cause DNA double strand breaks and oncogene activation. Iron may also play a role in the pathogenesis of rheumatic diseases and in predisposition to heart disease. High levels of iron can also cause diabetes with 2% of diabetics being hemochromatosis patients. High levels of iron may also affect the disease progression of many viral diseases. Individuals infected with such viruses as hepatitis (e.g., hepatitis B or C) or HIV should be tested for HFE mutations because of the impact increased iron stores have on the treatment and prognosis of such diseases.

Excessive iron stores and iron deposition is also a major contributing factor in the pathology and treatment of non-valvular heart disease. These conditions include dilated cardiomyopathy cased by deposition of iron in myocardial fibers; myocardial injury the product of anthracycline cardiomyopathy and re-perfusion injury. Increased iron stores may also be a contributing factor in myocardial infarction due to atherosclerosis. Some evidence suggests a significant increase in the incidence of reported heart disease in probands (cardiac symptoms-32%, insulin-dependent diabetes-18%, cardiac arrhythmia-17%, clinically significant coronary artery atherosclerosis-9%, and congestive heart failure-7%. Cardiac complications have been detected in 30% of patients. These include EKG abnormalities, congestive heart failure and cardiac arrhythmias. An increased frequency of HFE mutations in individuals with porphyria cutanea tarda indicates that HFE mutations may predipose an individual to developing this syndrome.

The effect of iron overload is irreparable damage to vital organs and a multiplicity of associated pathologies described above. The multiplicity of clinical symptoms (and associated pathologies) often causes misdiagnosis of hemochromatosis or failure to diagnose hemochromatosis.

Untreated hemochromatosis is characterized by iron overload of parenchymal cells, which is toxic and the probable cause of various complications including cirrhosis, and liver cancer, arthropathy, hypogonadotropic hypogonadism, marrow aplasia, skin disorders, diabetes mellitus, and cardiomyopathy. There are 1.5 to 2 million active cases in the U.S. of which 40% have progressive liver disease because they have not been properly diagnosed or treated.

In untreated hemochromatosis, iron is universally deposited in the hepatocytes of the liver. The iron is found primarily in the cytoplasm of hepatocytes, and by electron microscopy in lysosomal vacuoles, and in more severe cases iron has also been reported deposited in mitochondria. Other liver toxins such as alcohol, and hepatitis exacerbate the damage caused by the iron deposition. Patients with hemochromatosis are advised not to drink, because of increased liver damage, or to smoke, as iron deposition can also occur in the lungs.

Individuals which are homozygous (and to a lesser extent heterozygous) for an HFE mutation are at risk for developing increased levels of blood lead. Thus, it is important to identify heterozygous as well as homozygous patients.

Identification and detection of mutations in the HFE gene are critical to understanding the general mechanisms of iron disorders and diagnosing iron-related pathologies.

Nucleic Acid-based Assays for HFE Mutations

A biological sample containing RNA or DNA is obtained from an individual and the nucleic acid extracted. optionally, the nucleic acid is amplified according to standard procedures such as PCR. A nucleic acid polymorphism, e.g., a single base pair polymorphism, is detected using methods well known in the art of molecular biology. For example, a mutation is detected using a standard sequencing assay, nucleic acid hybridization, e.g., using standard Southern, Northern, or dot blot hybridization assay systems and an HFE-specific oligonucleotide probe, restriction enzyme fragment polymorphism analysis, oligonucleotide ligation assay (OLA; Nikerson et al., 1990, Nucl. Acids Res. 87:8923–8927), primer extension analysis (Nikiforov et al., 1994, Nucl. Acids Res. 22:4167–4175), single strand conformation polymorphism (SSCP) analysis, allele-specific PCR (Rust et al., 1993, Nucl. Acids Res. 6:3623–3629), denaturing gradient gel electrophoresis (DGGE), fluorescent probe melting curve analysis (Bernard et al., 1998, Am. J. Pathol. 153:1055–61), RNA mismatch cleavage assay, capillary hybridization, or TAQMAN™ assay (fluorogenic 5' nuclease assay) (PE Applied Biosystems, Foster City, Calif.). Nucleic acid hybridization assays are also carried out using a bioelectronic microchip technology known in the art, e.g., that described in Sosnowski et al., 1997, Proc. Natl. Acad. Sci. U.S.A. 94:1119–1123; Cheng et al. 1998, Nature Biotechnology 16:541–546; or Edman et al., 1997, Nucl. Acids Res. 25:4907–4914.

Detection of Mutations Using Antibodies and Other HFE Ligands

Anti-HFE antibodies are know in the art, e.g., those described by Feder et al., 1997, J. Biol. Chem. 272:14025–14028, or are obtained using standard techniques. Such antibodies can be polyclonal or monoclonal. Polyclonal antibodies can be obtained, for example, by the methods described in Ghose et al., Methods in Enzymology, Vol. 93, 326–327, 1983. An HFE polypeptide, or an antigenic fragment thereof, is used as an immunogen to stimulate the production of HFE-reactive polyclonal antibodies in the antisera of animals such as rabbits, goats, sheep, rodents and the like. HFE antibodies specific for mutated HFE gene products are raised by immunizing animals with a polypeptide spanning the mutation, e.g., a polypeptide which contains the mutations described herein. For example, the entire al domain of a mutant HFE gene product is used as an immunogen. Monoclonal antibodies are obtained by the process described by Milstein and Kohler in Nature, 256:495–97, 1975, or as modified by Gerhard, Monoclonal Antibodies, Plenum Press, 1980, pages 370–371. Hybridomas are screened to identify those producing antibodies that are highly specific for an HFE polypeptide containing a mutation characteristic of an iron metabolism abnormality or clinical hemochromatosis. Preferably, the antibody has an affinity of at least about 10=liters/mole, preferably at least 10≠liters/mole, more preferably at least 10[liters/mole, and most preferably, an affinity of at least about 10]liters/mole.

Antibodies specific for the wild type HFE can also be used to diagnose hemochromatosis or iron metabolism abnormalities. Such antibodies are also useful research tools to identify novel mutations indicative of iron disorders or hemochromatosis. A reduction in binding to a wild type HFE-specific antibody indicates the presence of a mutation. Antibody binding is detected using known methods. For example, an ELISA assay involves coating a substrate, e.g., a plastic dish, with an antigen, e.g., a patient-derived biological sample containing an HFE gene product. An antibody preparation is then added to the well. Antibodies specific for a mutant HFE gene product bind or fail to bind to a patient-derived sample in the well. Non-binding material is washed away and a marker enzyme e.g., horse radish peroxidase or alkaline phosphatase, coupled to a second antibody directed against the antigen-specific primary antibody is added in excess and the nonadherent material is washed away. An enzyme substrate is added to the well and the enzyme catalyzed conversion is monitored as indicative of presence of the mutation. Antibodies are also labelled with various sizes of colloidal gold particles or latex particles for detection of binding.

The invention employs not only intact monoclonal or polyclonal antibodies, but also an immunologically-active antibody fragment, for example, a Fab or (Fab)$_2$ fragment; an antibody heavy chain, an antibody light chain; a genetically engineered single-chain Fv molecule (Ladner et al., U.S. Pat. No. 4,946,778).

EXAMPLE 1

Selection and Characterization of Subjects

All individuals studied were Caucasians, 18 years of age or older, and from central Alabama. Twenty probands were identified that were either heterozygous for C282Y or H63D, or lacked these mutations. Hemochromatosis is typically diagnosed by detecting elevated saturation of transferrin, with elevated serum ferritin levels, combined with liver biopsy. Each proband patient described below was previously diagnosed to have hemochromatosis by the working diagnostic criterion for hemochromatosis of the American College of Pathologists (elevated fasting transferrin saturation of greater than 60% saturation for males and greater than 50% saturation for females) on at least two occasions in the absence of other known causes. Probands were interviewed regarding their general medical history, diet (including estimated iron content and ethanol consumption), medicinal iron use, receipt of blood transfusion, prior significant hemorrhage, blood donation for transfusion and/or therapeutic phlebotomy, and pregnancy and lactation. Each proband was also evaluated for viral hepatitis B and C and other hepatic disorders, excess ethanol intake, and hereditary, and acquired anemia. Iron overload was defined as evidence of systemic iron overload demonstrated by otherwise unexplained elevated serum is ferritin concentration ($\geq$300 ng/mL in men, $\geq$200 ng/mL in women), increased hepatic iron content determined using hepatic biopsy specimens, or iron >4 g mobilized by phlebotomy. Complications of iron overload were evaluated and treated, and therapeutic phlebotomy was performed using standard methods. HFE mutation analysis for C282Y and H63D and human leukocyte antigen (HLA) immunophenotyping or molecular typing were performed using known methods. In some family members, HLA haplotyping had been performed previously for other disease associations, or their HLA type could be deduced from analysis of their kinship and HFE genotyping results. Measurement of serum iron and other clinical laboratory parameters and analysis of hepatic biopsy specimens were performed using routine methods. Control subjects (n=176) who were in apparently good health and were unrelated to the hemochromatosis probands were recruited from the general population. Iron parameters were measured and HLA typing was performed in two control subjects after HFE genotyping revealed that they had the S65C mutation.

EXAMPLE 2

HFE Gene Analysis

PCR amplification was used to detect mutations. Genomic DNA was prepared from peripheral blood buffy coat or saliva using the QIAmpBlood Kit (QIAGEN, Valencia, Calif.) or FTA Paper and FTA purification reagent (Fitzco Inc., Maple Plain, Minn.), respectively. Fragments were amplified from genomic DNA using eLONGase (Life Technologies, Gaithersburg, Md.) or HotStarTaq DNA polymerase (QIAGEN, Valencia, Calif.). Primers used to amplify each exon are shown in Table 3.

TABLE 4

Human HFE genomic DNA (SEQ ID NO:27; GENBANK ® Accession No. Z92910)

|  |  |  |  |  |  |
|---:|---|---|---|---|---|
| 1 | ggatccttta | accgaggaga | ttattatagc | cggagctctg | aagcagcaat ctcagttctt |
| 61 | gtgatagtga | gcaaagaact | acaaactaac | accaaaatgc | aagcttaaag caaagtttat |
| 121 | tgaagcacaa | taatacactc | tgagggacag | cgggcttatt | tctgcgaagt gaactcagca |
| 181 | cttcttaca | gagctcaagg | tgcttttatg | gggtttgtgg | ggaggagttg aggtttgggc |
| 241 | tgtatctgag | tgacaggatg | atgttatttg | attgaagttt | atagctatac aatctaaaat |
| 301 | taaactgtgc | atggtcttac | ctataatttg | ttaagaaaag | cctcccaggg atgggggggc |
| 361 | aaaactgtat | gtaaattcta | ttataatgat | ggcatgatga | acttggggtg aacttgaaga |
| 421 | caggcttttg | tgttgttggg | catgtgccac | cttagggaat | ttccacctgt accctccttt |
| 481 | ctctttctcc | aggatatttt | ggccacagac | tttatcataa | actccatccc ttagggtggc |
| 541 | attagggtag | tcttgggcct | gaatttaggt | gggccagtgg | ctgtcttagt gacagccttt |
| 601 | ccgctctctt | ctgtcatccc | ctcccaactg | ctaatgtcta | actacctaac aattacccat |
| 661 | taaatcagtg | tgtctggggt | taggagcagg | cctcaatatg | tttaatcatt ctccagataa |
| 721 | tcccaatact | gtaaagtttg | tgaaacactt | gtcagataat | tcaattatga aggctgtgga |
| 781 | acgtgtttca | gtaggatcta | attggttaat | gttatgactt | aattaatttg aatcaaaaaa |
| 841 | caaaatgaaa | aagctttata | tttctaagtc | aaataagaca | taagttggtc taaggttgag |
| 901 | ataaaattt | taaatgtatg | attgaatttt | gaaaatcata | aatatttaaa tatctaaagt |

TABLE 4-continued

Human HFE genomic DNA (SEQ ID NO:27; GENBANK ® Accession No. Z92910)

```
 961  tcagatcaga acattgcgaa gctactttcc ccaatcaaca acaccccttc aggatttaaa
1021  aaccaagggg gacactggat cacctagtgt ttcacaagca ggtaccttct gctgtaggag
1081  agagagaact aaagttctga aagacctgtt gcttttcacc aggaagtttt actgggcatc
1141  tcctgagcct aggcaatagc tgtagggtga cttctggagc catcccgtt tccccgcccc
1201  ccaaaagaag cggagattta acggggacgt gcggccagag ctggggaaat gggcccgcga
1261  gccaggccgg cgcttctcct cctgatgctt ttgcagaccg cggtcctgca ggggcgcttg
1321  ctgcgtgagt ccgagggctg cgggcgaact aggggcgcgg cggggtgga aaaatcgaaa
1381  ctagcttttt ctttgcgctt gggagtttgc taactttgga ggacctgctc aacccaatcc
1441  gcaagcccct ctccctactt tctgcgtcca gacccgtga gggagtgcct accactgaac
1501  tgcagatagg ggtccctcgc cccaggacct gcccctccc ccggctgtcc cggctctgcg
1561  gagtgacttt tggaaccgcc cactcccttc ccccaactag aatgctttta aataaatctc
1621  gtagttcctc acttgagctg agctaagcct ggggctcctt gaacctggaa ctcgggttta
1681  tttccaatgt cagctgtgca gtttttccc cagtcatctc caaacaggaa gttcttccct
1741  gagtgcttgc cgagaaggct gagcaaaccc acagcaggat ccgcacgggg tttccacctc
1801  agaacgaatg cgttgggcgg tgggggcgcg aaagagtggc gttggggatc tgaattcttc
1861  accattccac ccacttttgg tgagacctgg ggtggaggtc tctagggtgg gaggctcctg
1921  agagaggcct acctcgggcc tttccccact cttggcaatt gttcttttgc ctggaaaatt
1981  aagtatatgt tagttttgaa cgtttgaact gaacaattct cttttcggct aggctttatt
2041  gatttgcaat gtgctgtgta attaagaggc ctctctacaa agtactgata atgaacatgt
2101  aagcaatgca ctcacttcta agttacattc atatctgatc ttatttgatt ttcactaggc
2161  atagggaggt aggagctaat aatacgttta ttttactaga agttaactgg aattcagatt
2221  atataactct tttcaggtta caaagaacat aaataatctg gttttctgat gttatttcaa
2281  gtactacagc tgcttctaat cttagttgac agtgattttg ccctgtagtg tagcacagtg
2341  ttctgtgggt cacacgccgg cctcagcaca gcactttgag ttttggtact acgtgtatcc
2401  acattttaca catgacaaga atgaggcatg gcacggcctg cttcctggca aatttattca
2461  atggtacacg gggctttggt ggcagagctc atgtctccac ttcatagcta tgattcttaa
2521  acatcacact gcattagagg ttgaataata aaatttcatg ttgagcagaa atattcattg
2581  tttacaagtg taaatgagtc ccagccatgt gttgcactgt tcaagcccca agggagagag
2641  cagggaaaca agtctttacc ctttgatatt ttgcattcta gtgggagaga tgacaataag
2701  caaatgagca gaaagatata caacatcagg aaatcatggg tgttgtgaga agcagagaag
2761  tcagggcaag tcactctggg gctgacactt gagcagagac atgaaggaaa taagaatgat
2821  attgactggg agcagtattt cccaggcaaa ctgagtgggc ctggcaagtt ggattaaaaa
2881  gcgggttttc tcagcactac tcatgtgtgt gtgtgtgggg gggggggcgg cgtgggggtg
2941  ggaaggggga ctaccatctg catgtaggat gtctagcagt atcctgtcct ccctactcac
3001  taggtgctag gagcactccc ccagtcttga caaccaaaaa tgtctctaaa ctttgccaca
3061  tgtcacctag tagacaaact cctggttaag aagctcgggt tgaaaaaaat aaacaagtag
3121  tgctggggag tagaggccaa gaagtaggta atgggctcag aagaggagcc acaaacaagg
```

TABLE 4-continued

Human HFE genomic DNA (SEQ ID NO:27; GENBANK ® Accession No. Z92910)

| | |
|---|---|
| 3181 | ttgtgcaggc gcctgtaggc tgtggtgtga attctagcca aggagtaaca gtgatctgtc |
| 3241 | acaggctttt aaaagattgc tctggctgct atgtggaaag cagaatgaag ggagcaacag |
| 3301 | taaaagcagg gagcccagcc aggaagctgt tacacagtcc aggcaagagg tagtggagtg |
| 3361 | ggctgggtgg aacagaaaa gggagtgaca aaccattgtc tcctgaatat attctgaagg |
| 3421 | aagttgctga aggattctat gttgtgtgag agaaagagaa gaattggctg ggtgtagtag |
| 3481 | ctcatgccaa ggaggaggcc aaggagagca gattcctgag ctcaggagtt caagaccagc |
| 3541 | ctgggcaaca cagcaaaacc ccttctctac aaaaaataca aaaattagct gggtgtggtg |
| 3601 | gcatgcacct gtgatcctag ctactcggga ggctgaggtg gagggtattg cttgagccca |
| 3661 | ggaagttgag gctgcagtga gccatgactg tgccactgta cttcagccta ggtgacagag |
| 3721 | caagaccctg tctcccctga ccccctgaaa aagagaagag ttaaagttga ctttgttctt |
| 3781 | tattttaatt ttattggcct gagcagtggg gtaattggca atgccatttc tgagatggtg |
| 3841 | aaggcagagg aaagagcagt ttggggtaaa tcaaggatct gcatttggac atgttaagtt |
| 3901 | tgagattcca gtcaggcttc caagtggtga ggccacatag gcagttcagt gtaagaattc |
| 3961 | aggaccaagg cagggcacgg tggctcactt ctgtaatccc agcactttg tggctgaggc |
| 4021 | aggtagatca tttgaggtca ggagtttgag acaagcttgg ccaacatggt gaaaccccat |
| 4081 | gtctactaaa aatacaaaaa ttagcctggt gtggtggcgc acgcctatag tcccaggttt |
| 4141 | tcaggaggct taggtaggag aatcccttga acccaggagg tgcaggttgc agtgagctga |
| 4201 | gattgtgcca ctgcactcca gcctgggtga tagagtgaga ctctgtctca aaaaaaaaa |
| 4261 | aaaaaaaaa aaaaaaaaa aactgaagga attattcctc aggatttggg tctaatttgc |
| 4321 | cctgagcacc aactcctgag ttcaactacc atggctagac acacttaac attttctaga |
| 4381 | atccaccagc tttagtggag tctgtctaat catgagtatt ggaataggat ctgggggcag |
| 4441 | tgaggggtg gcagccacgt gtggcagaga aaagcacaca aggaaagagc acccaggact |
| 4501 | gtcatatgga agaaagacag gactgcaact caccccttcac aaaatgagga ccagacacag |
| 4561 | ctgatggtat gagttgatgc aggtgtgtgg agcctcaaca tcctgctccc ctcctactac |
| 4621 | acatggttaa ggcctgttgc tctgtctcca ggttcacact ctctgcacta cctcttcatg |
| 4681 | ggtgcctcag gcaggacct tggtctttcc ttgtttgaag ctttgggcta cgtggatgac |
| 4741 | cagctgttcg tgttctatga tcatgagagt cgccgtgtgg agccccgaac tccatgggtt |
| 4801 | tccagtagaa tttcaagcca gatgtggctg cagctgagtc agagtctgaa agggtgggat |
| 4861 | cacatgttca ctgttgactt ctggactatt atggaaaatc acaaccacag caagggtatg |
| 4921 | tggagagggg gcctcacctt cctgaggttg tcagagcttt tcatcttttc atgcatcttg |
| 4981 | aaggaaacag ctggaagtct gaggtcttgt gggagcaggg aagagggaag gaatttgctt |
| 5041 | cctgagatca tttggtcctt ggggatggtg gaaataggga cctattcctt tggttgcagt |
| 5101 | taacaaggct ggggattttt ccagagtccc acaccctgca ggtcatcctg ggctgtgaaa |
| 5161 | tgcaagaaga caacagtacc gagggctact ggaagtacgg gtatgatggg caggaccacc |
| 5221 | ttgaattctg ccctgacaca ctggattgga gagcagcaga acccaggggcc tggcccacca |
| 5281 | agctggagtg ggaaaggcac aagattcggg ccaggcagaa cagggcctac ctggagaggg |
| 5341 | actgccctgc acagctgcag cagttgctgg agctggggag aggtgttttg gaccaacaag |
| 5401 | gtatggtgga aacacacttc tgcccctata ctctagtggc agagtggagg aggttgcagg |

TABLE 4-continued

Human HFE genomic DNA (SEQ ID NO:27; GENBANK ® Accession No. Z92910)

```
5461  gcacggaatc cctggttgga gtttcagagg tggctgaggc tgtgtgcctc tccaaattct
5521  gggaagggac tttctcaatc ctagagtctc taccttataa ttgagatgta tgagacagcc
5581  acaagtcatg ggtttaattt cttttctcca tgcatatggc tcaaagggaa gtgtctatgg
5641  cccttgcttt ttatttaacc aataatcttt tgtatattta tacctgttaa aaattcagaa
5701  atgtcaaggc cgggcacggt ggctcacccc tgtaatccca gcactttggg aggccgaggc
5761  gggtggtcac aaggtcagga gtttgagacc agcctgacca acatggtgaa acccgtctct
5821  aaaaaaatac aaaaattagc tggtcacagt catgcgcacc tgtagtccca gctaattgga
5881  aggctgaggc aggagcatcg cttgaacctg ggaagcggaa gttgcactga gccaagatcg
5941  cgccactgca ctccagccta ggcagcagag tgagactcca tcttaaaaaa aaaaaaaaa
6001  aaaagagaa ttcagagatc tcagctatca tatgaatacc aggacaaaat atcaagtgag
6061  gccacttatc agagtagaag aatcctttag gttaaaagtt tctttcatag aacatagcaa
6121  taatcactga agctacctat cttacaagtc cgcttcttat aacaatgcct cctaggttga
6181  cccaggtgaa actgaccatc tgtattcaat cattttcaat gcacataaag ggcaattta
6241  tctatcagaa caaagaacat gggtaacaga tatgtatatt tacatgtgag gagaacaagc
6301  tgatctgact gctctccaag tgacactgtg ttagagtcca atcttaggac acaaaatggt
6361  gtctctcctg tagcttgttt ttttctgaaa agggtatttc cttcctccaa cctatagaag
6421  gaagtgaaag ttccagtctt cctggcaagg gtaaacagat cccctctcct catccttcct
6481  ctttcctgtc aagtgcctcc tttggtgaag gtgacacatc atgtgacctc ttcagtgacc
6541  actctacggt gtcgggcctt gaactactac ccccagaaca tcaccatgaa gtggctgaag
6601  gataagcagc caatggatgc caaggagttc gaacctaaag acgtattgcc caatggggat
6661  gggacctacc agggctggat aaccttggct gtaccccctg gggaagagca gagatatacg
6721  tgccaggtgg agcacccagg cctggatcag cccctcattg tgatctgggg tatgtgactg
6781  atgagagcca ggagctgaga aaatctattg ggggttgaga ggagtgcctg aggaggtaat
6841  tatggcagtg agatgaggat ctgctctttg ttaggggatg ggctgagggt ggcaatcaaa
6901  ggctttaact tgctttttct gttttagagc cctcaccgtc tggcacccta gtcattggag
6961  tcatcagtgg aattgctgtt tttgtcgtca tcttgttcat tggaattttg ttcataatat
7021  taaggaagag gcagggttca agtgagtagg aacaagggg aagtctctta gtacctctgc
7081  cccagggcac agtgggaaga ggggcagagg ggatctggca tccatgggaa gcatttttct
7141  catttatatt ctttggggac accagcagct ccctgggaga cagaaaataa tggttctccc
7201  cagaatgaaa gtctctaatt caacaaacat cttcagagca cctactattt tgcaagagct
7261  gtttaaggta gtacagggc tttgaggttg agaagtcact gtggctattc tcagaaccca
7321  aatctggtag ggaatgaaat tgatagcaag taaatgtagt taagaagac cccatgaggt
7381  cctaaagcag gcaggaagca aatgcttagg gtgtcaaagg aaagaatgat cacattcagc
7441  tggggatcaa gatagccttc tggatcttga aggagaagct ggattccatt aggtgaggtt
7501  gaagatgatg ggaggtctac acagacggag caaccatgcc aagtaggaga gtataaggca
7561  tactgggaga ttagaaataa ttactgtacc ttaaccctga gtttgcttag ctatcactca
7621  ccaattatgc atttctaccc cctgaacatc tgtggtgtag ggaaaagaga atcagaaaga
```

TABLE 4-continued

Human HFE genomic DNA (SEQ ID NO:27; GENBANK ® Accession No. Z92910)

```
7681  agccagctca tacagagtcc aagggtctttt tgggatattg ggttatgatc actggggtgt
7741  cattgaagga tcctaagaaa ggaggaccac gatctccctt atatggtgaa tgtgttgtta
7801  agaagttaga tgagaggtga ggagaccagt tagaaagcca ataagcattt ccagatgaga
7861  gataatggtt cttgaaatcc aatagtgccc aggtctaaat tgagatgggt gaatgaggaa
7921  aataaggaag agagaagagg caagatggtg cctaggtttg tgatgcctct ttcctgggtc
7981  tcttgtctcc acaggaggag ccatgggcca ctacgtctta gctgaacgtg agtgacacgc
8041  agcctgcaga ctcactgtgg gaaggagaca aaactagaga ctcaaagagg gagtgcattt
8101  atgagctctt catgtttcag gagagagttg aacctaaaca tagaaattgc ctgacgaact
8161  ccttgatttt agccttctct gttcatttcc tcaaaaagat ttccccatttt aggtttctga
8221  gttcctgcat gccggtgatc cctagctgtg acctctcccc tggaactgtc tctcatgaac
8281  ctcaagctgc atctagaggc ttccttcatt tcctccgtca cctcagagac atacacctat
8341  gtcatttcat ttcctatttt tggaagagga ctccttaaat ttgggggact tacatgattc
8401  attttaacat ctgagaaaag ctttgaaccc tgggacgtgg ctagtcataa cttaccaga
8461  tttttacaca tgtatctatg catttctgg acccgttcaa ctttttccttt gaatcctctc
8521  tctgtgttac ccagtaactc atctgtcacc aagccttggg gattcttcca tctgattgtg
8581  atgtgagttg cacagctatg aaggctgtac actgcacgaa tggaagaggc acctgtccca
8641  gaaaaagcat catggctatc tgtgggtagt atgatgggtg ttttttagcag gtaggaggca
8701  aatatcttga aaggggttgt gaagaggtgt tttttctaat tggcatgaag gtgtcataca
8761  gatttgcaaa gtttaatggt gccttcattt gggatgctac tctagtattc cagacctgaa
8821  gaatcacaat aatttttctac ctggtctctc cttgttctga taatgaaaat tatgataagg
8881  atgataaaag cacttacttc gtgtccgact ctttctgagca cctacttaca tgcattactg
8941  catgcacttc ttacaataat tctatgagat aggtactatt atccccatttt ctttttttaaa
9001  tgaagaaagt gaagtaggcc gggcacggtg gctcacgcct gtaatcccag cactttggga
9061  ggccaaagcg gtggatcac gaggtcagga gatcgagacc atcctggcta acatggtgaa
9121  accccatctc taataaaaat acaaaaaatt agctgggcgt ggtggcagac gcctgtagtc
9181  ccagctactc ggaaggctga ggcaggagaa tggcatgaac ccaggaggca gagcttgcag
9241  tgagccgagt ttgcgccact gcactccagc ctaggtgaca gagtgagact ccatctcaaa
9301  aaaataaaaat aaaaataaa aaatgaaaa aaaaaagaaa gtgaagtata gagtatctca
9361  tagtttgtca gtgatagaaa caggtttcaa actcagtcaa tctgaccgtt tgatacatct
9421  cagacaccac tacattcagt agtttagatg cctagaataa atagagaagg aaggagatgg
9481  ctcttctctt gtctcattgt gtttcttctg aatgagcttg aatcacatga aggggaacag
9541  cagaaaacaa ccaactgatc ctcagctgtc atgtttcctt taaaagtccc tgaaggaagg
9601  tcctggaatg tgactcccttt gctcctctgt tgctctcttt ggcattcatt tctttggacc
9661  ctacgcaagg actgtaattg gtggggacag ctagtggccc tgctgggctt cacacacggt
9721  gtcctcccta ggccagtgcc tctgagtca gaactctggt ggtatttccc tcaatgaagt
9781  ggagtaagct ctctcatttt gagatggtat aatggaagcc accaagtggc ttagaggatg
9841  cccaggtcct tccatggagc cactgggggtt ccggtgcaca ttaaaaaaaa aatctaacca
9901  ggacattcag gaattgctag attctgggaa atcagttcac catgttcaaa agagtctttt
```

TABLE 4-continued

Human HFE genomic DNA (SEQ ID NO:27; GENBANK ® Accession No. Z92910)

```
 9961 tttttttttt gagactctat tgcccaggct ggagtgcaat ggcatgatct cggctcactg
10021 taacctctgc ctcccaggtt caagcgattc tcctgtctca gcctcccaag tagctgggat
10081 tacaggcgtg caccaccatg cccggctaat ttttgtattt ttagtagaga cagggtttca
10141 ccatgttggc caggctggtc tcgaactctc ctgacctcgt gatccgcctg cctcggcctc
10201 ccaaagtgct gagattacag gtgtgagcca ccctgcccag ccgtcaaaag agtcttaata
10261 tatatatcca gatggcatgt gtttactta tgttactaca tgcacttggc tgcataaatg
10321 tggtacaagc attctgtctt gaagggcagg tgcttcagga taccatatac agctcagaag
10381 tttcttcttt aggcattaaa ttttagcaaa gatatctcat ctcttctttt aaaccatttt
10441 cttttttgt ggttagaaaa gttatgtaga aaaagtaaa tgtgatttac gctcattgta
10501 gaaaagctat aaaatgaata caattaaagc tgttatttaa ttagccagtg aaaaactatt
10561 aacaacttgt ctattacctg ttagtattat tgttgcatta aaaatgcata tactttaata
10621 aatgtacatt gtattgtata ctgcatgatt ttattgaagt tcttgttcat cttgtgtata
10681 tacttaatcg ctttgtcatt ttggagacat ttattttgct tctaatttct ttacatttg
10741 tcttacggaa tattttcatt caactgtggt agccgaatta atcgtgtttc ttcactctag
10801 ggacattgtc gtctaagttg taagacattg gttattttac cagcaaacca ttctgaaagc
10861 atatgacaaa ttatttctct cttaatatct tactatactg aaagcagact gctataaggc
10921 ttcacttact cttctacctc ataaggaata tgttacaatt aatttattag gtaagcattt
10981 gttttatatt ggttttattt cacctgggct gagatttcaa gaaacacccc agtcttcaca
11041 gtaacacatt tcactaacac atttactaaa catcagcaac tgtggcctgt taatttttt
11101 aatagaaatt ttaagtcctc attttctttc ggtgtttttt aagcttaatt tttctggctt
11161 tattcataaa ttcttaaggt caactacatt tgaaaaatca aagacctgca ttttaaattc
11221 ttattcacct ctggcaaaac cattcacaaa ccatggtagt aaagagaagg gtgacacctg
11281 gtggccatag gtaaatgtac cacggtggtc cggtgaccag agatgcagcg ctgagggttt
11341 tcctgaaggt aaaggaataa agaatgggtg gaggggcgtg cactggaaat cacttgtaga
11401 gaaaagcccc tgaaaatttg agaaaacaaa caagaaacta cttaccagct atttgaattg
11461 ctggaatcac aggccattgc tgagctgcct gaactgggaa cacaacagaa ggaaaacaaa
11521 ccactctgat aatcattgag tcaagtacag caggtgattg aggactgctg agaggtacag
11581 gccaaaattc ttatgttgta ttataataat gtcatcttat aatactgtca gtattttata
11641 aaacattctt cacaaactca cacacattta aaaacaaaac actgtctcta aaatccccaa
11701 attttcata aactcagttt taaactaact ttttttcaaa ccacaatctg atttaacaat
11761 gactatcatt taaatatttc tgactttcaa attaaagatt ttcacatgca ggctgatatt
11821 tgtaattgtg attctctctg taggctttgg gtaatgtg ttcttttcct tttttgcatc
11881 agcgattaac ttctacactc taacatgtag aatgttacta caatattaaa gtattttgta
11941 tgacaatttt atttgaaagc ctaggatgcg ttgacatcct gcatgcattt attacttgat
12001 atgcatgcat tctggtatct caagcattct atttctgagt aattgtttaa ggtgtagaag
12061 agatagatat ggtggatttg gagttgatac ttatatattt tctatttctt ggatggatga
12121 atttgtacat taaaagttt ccatgg
```

Exon 1 spans nt 1028–1324, inclusive; exon 2 spans nt 4652–4915, inclusive; exon 3 spans nt 5125–5400, inclusive; exon 4 spans nt 6494–6769, inclusive; exon 5 spans nt 6928–7041, inclusive; exon 6 spans nt 7995–9050, inclusive, and exon 7 spans nt 10206–10637, inclusive. Intron 4 spans nt 6770–6927, inclusive, and intron 5 spans nt 7042–7994, inclusive.

Total RNA for the RT-PCR was prepared from 1.5 mL of whole blood using the RNeasy Blood Kit (QIAGEN, Valencia, Calif.). Total messenger RNA encoding the HFE gene was transcribed and amplified with the primers shown above using standard methods, e.g., the Superscript ONE-STEP RT- PCR System (Life Technologies, Gaithersburg, MD). The amplified product was directly subcloned into the pCR2.1-TOPO vector and transfected into TOP 10 bacteria (Invitrogen, Carlsbad, Calif.). Plasmid DNAs isolated from the subcloning were prepared with the UltraClean Mini Prep Kit (Mo Bio, Solana Beach, Calif.) and sequenced.

DNA sequencing was performed using the ABI Prism BigDye Terminator Cycle Sequencing Ready Reaction Kit (PE Applied Biosystems, Foster City, Calif.) and analyzed on an ABI Prism 377.

To detect mutations in exon 2 of the HFE gene, the genomic DNA of probands and normal control subjects were amplified and subjected to a dot blot hybridization assay. 1.0 µl of each resulting PCR product was then applied to a Magna Graph nylon membrane (MSI, Westboro, Mass.). The membranes were treated with 0.5 N NaOH/1.5 M NaCl to denature the DNA, neutralized with 0.5 M Tris-HCl (pH 8.0)/1.5 M NaCl, and rinsed with 2×SSC (1 ×SSC=0.15 M NaCl/0.015 M sodium citrate, pH 7.0). The DNAs were fixed on the membrane by UV irradiation using a Stratalinker 1800 (Stratagene, Inc., La Jolla, Calif.). The ECL 3'-oligolabelling and detection system (Amersham, Arlington Heights, Ill.) was used for synthesis of labeled oligonucleotide probes, hybridization, and signal detection. The oligonucleotide sequences used to detect each point mutation were (substituted bases are shown as upper case

TABLE 5

Oligonucleotide Probes

| Point Mutation | Oligonucleotide |
|---|---|
| G93R mutation | gtctgaaaCggtgggat (SEQ ID NO:28) |
| I105T mutation | acttctggactaCtatgg (SEQ ID NO:29) |
| S65C mutation | atcatgagTgtcgccgt (SEQ ID NO: 30) |

For signal detection, each oligonucleotide was labeled with fluorescein-11-dUTP using terminal deoxynucleotidyl transferase according to the manufacturer's instructions (Amersham Ltd., Arlington Heights, Ill.). The membranes were prehybridized in 5×SSC, 0.1% Hybridization buffer component, 0.02% SDS, 5% LiquidBlock at 42° C. for approximately 2 hours. Labelled oligonucleotide probes were added to individual bags containing the membranes and prehybridization buffer and incubated at 42° C. overnight. The blots were washed twice with 5×SSC, 0.1% SDS for 5 minutes at room temperature. Stringency washes for hybridization with oligonucleotides having the sequence of SEQ ID NO: 30 or 28 were performed twice in 0.2×SSC/ 0.1% SDS for 15 minutes at 42° C. Membranes probed with an oligonucleotide having the sequence of SEQ ID NO:29 was washed twice under less stringent conditions (0.5×SSC/ 0.1% SDS, 15 minutes at 42° C.). Detection of a fluorescent signal was performed according to standard methods.

EXAMPLE 3

Characterization of Probands

The mean age of the twenty probands was 44±11 years (range 27–62 years); thirteen (65.0%) were men and seven (35.0%) were women. Eleven had iron overload. One had hepatic cirrhosis, two had diabetes mellitus, four had arthropathy, and two had hypogonadotrophic hypogonadism. One proband also had hereditary stomatocytosis, another had beta-thalassemia trait, a third had ethanol intake >60 g daily, and a fourth had porphyria cutanea tarda. No proband had evidence of excess oral or parenteral iron intake, or of viral hepatitis B or C. At diagnosis of hemochromatosis, evaluation for common HFE mutations revealed that eleven probands were C282Y heterozygotes, five were H63D heterozygotes, and four did not inherit C282Y or H63D.

The mean age of the initial 176 control subjects was 52±15 years (range 18–86 years); 79 (44.9%) were men and 97 (55.1%) were women. There was no significant difference in the mean ages of men and women. Frequencies of HFE genotypes among the control subjects are shown in Table 6. These values are similar to those previously reported from normal persons from the same geographic area.

TABLE 6

Frequencies of HFE Genotypes in Alabama Subjects.

| HFE Genotype | Hemochromatosis Probands with "Atypical" HFE Genotypes, % (n) | Normal Control Subjects, % (n) |
|---|---|---|
| wt/wt | 15.00 (3) | 60.23 (106) |
| C282Y/wt | 45.00 (9) | 13.06 (23) |
| H63D/wt | 20.00 (4) | 15.34 (27) |
| S65C/wt | 5.00 (1) | 1.14 (2) |
| C282Y/S65C | 5.00 (1) | 0 |
| C282Y/G93R | 5.00 (1) | 0 |
| H63D/I105T | 5.00 (1) | 0 |
| H63D/C282Y | 0 | 6.82 (12) |
| H63D/H63D | 0 | 3.41 (6) |

Results are expressed as percentage (n). The wild-type (wt) allele was defined as the HFE configuration in which the mutations C282Y, H63D, S65C, I105T, or G93R were not detected.

EXAMPLE 4

Identification of Novel HFE Mutations in Hemochromatosis Probands

Figure 2:
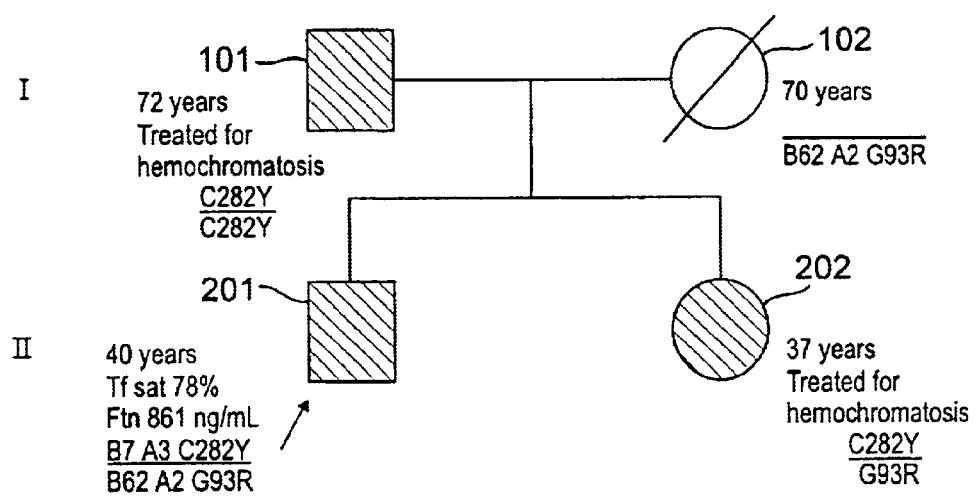
FIG. 2 is a diagram of the family of proband 2 (HFE genotype C282Y/G93R). Symbols and abbreviations are the same as those described for FIG. 1. Proband 2 is indicated with an arrow. G93R, C282Y, and wt alleles are known to exist only on separate chromosomes. The father and sister of the proband are being treated for hemochromatosis.

The following novel mutations (missense mutations) were identified in probands 1 and 2: exon 2, nt 314T→C (I105T), and exon 2, nt 277G→C (G93R), respectively (Table 7; FIGS. 1 and 2). Probands 3 and 4 had a S65C mutation The S65C mutation has been observed in hemochromatosis patients but has not been deemed to be indicative of a disease state. In contrast, the data presented herein indicate that the S65C mutation is diagnostic of a disease state. This result is surprising in view of earlier observations. Other than C282Y or H63D, no HFE exon mutations were detected in the remaining sixteen of the twenty probands (Table 6). Nine probands were heterozygous for a base-pair change at intron 2, nt 4919T/C (SEQ ID NO:27); two probands were homozygous for this base-pair change. Heterozygosity for a base-pair change in intron 4 (nt 6884T→C) was detected only in probands 3 and 4, both of whom also inherited S65C. One proband was heterozygous for a base-pair change at intron 5, nt 7055A→G.

Using dot blot methodology, heterozygosity for the S65C mutation was detected in two of 176 normal control subjects (Table 6). The G93R or I105T mutations were not detected in normal control subjects (Tables 6 and 8).

EXAMPLE 5

Association of Novel HFE Coding Region Mutations to C282Y and H63D and HFE Intron Alleles In proband 1, two mutations of exon 2 (H63D and I105T) were detected. After subcloning the genomic fragment, the subclones revealed that these mutations occurred on separate chromosomes; this observation was confirmed by family studies indicating segregation of I105T and H63D (FIG. 1). In proband 2 (HFE genotype C282Y/G93R), RT-PCR analysis (with subsequent subcloning and sequencing) revealed that these HFE mutations occurred on separate chromosomes. Family studies of proband 3 (HFE genotype C282Y/S65C) indicated that the C282Y and S65C HFE alleles segregated independently, establishing their occurrence on separate chromosomes (Table 7, FIG. 3).

In proband 1 (HFE genotype H63D/I105T), the I105T mutation was co-inherited with HLA-A3, B7. In probands 3 and 4 and their respective families, S65C was inherited on the same chromosome as HLA-A32, indicating that HLA-A32 is a marker for chromosomes bearing the S65C mutation, and individuals with HLA-A32 have an increased risk for developing hemochromatosis. The G93R mutation is associated with HLA-A2, and individuals with that haplotype have an increased risk for developing hemochromatosis. The I105T mutation is associated with HLA-A3, e.g., HLA-A3, B7, and individuals with that haplotype have an increased risk for developing hemochromatosis. Among twenty probands tested, the nucleotide polymorphism in

TABLE 7

Phenotypes and Uncommon HFE Genotype in Alabama Subjects*

| Subject† | Age (years), Sex | HFE Genotype | HLA Type | Transferrin Saturation % | Serum Ferritin, ng/mL | Hepatocyte Iron Grade | Phlebotomy, Units |
|---|---|---|---|---|---|---|---|
| Proband 1 | 52 M | H63D/I105T | A2, 3; B7, 7 | 62 | 868 | 2+ | 20 |
| Proband 2‡ | 40 M | C282Y/G93R | A2, 3; B7, 62 | 78 | 861 | 4+ | 34 |
| Proband 3§ | 47 F | C282Y/S65C | A2, 32; B8, 44; Bw4, 6; Cw5, 7 | 90 | 281 | 3+ | 37 |
| Proband 4** | 81 F | S65C/wt | A2, 32; B14, 62 | 100 | 5,135 | N.D. | 37 |
| Normal Control 1 | 28 M | S65C/wt | A2, 31; B35, 60 | 28 | 141 | N.D. | N.D. |
| Normal Control 2 | 69 M | S65C/wt | A24, 26; B8, B37; Bw4, 6; Cw6, 5 (or 7) | 42 | 747 | 2+ | N.D. |

*Serum transferrin saturation, serum ferritin concentration, and percutaneous hepatic biopsy were performed before therapeutic phlebotomy was initiated. Reference ranges for these parameters are 15–45%; 20–300 ng/mL (men) and 20–200 ng/mL (women); and 0–1+, respectively. Iron depletion (serum ferritin ≦ 20 ng/mL) was induced by removing the indicated numbers of units of blood. None of these persons had evidence of hepatic cirrhosis, diabetes mellitus, hemochromatosis-associated arthropathy, hypogonadotrophic hypogonadism, other endocrinopathy, or cardiomyopathy.
N.D. = not done. The mutations indicated are exon 4, nt 845G→A (C282Y); exon 2, nt 187C→G (H63D); exon 2, nt 314T→C (I105T); exon 2, nt 277G→C (G93R); and exon 2, nt 193A→T (S65C). The wild-type (wt) allele was defined as an HFE allele in which the mutations C282Y, H63D, S65C, I105T, or G93R were not detected.
†Countries of origin: Probands 1 and 2, England; Proband 3, Wales, England, and Americas (Cherokee); Proband 4, England and Ireland; Normal Control 1, England; Normal Control 2, The Netherlands.
‡The father and sister of Proband 2 are presently undergoing therapy for hemochromatosis and iron overload, but their clinical and genetic data were unavailable.
§Proband 3 had porphyria cutanea tarda alleviated with therapeutic phlebotomy.
**Proband 4 had hereditary stomatocytosis unaffected by phlebotomy treatments. 37 units of blood were removed by phlebotomy before treatment was discontinued due to stroke apparently unrelated to anemia or iron overload (post-treatment serum ferritin 1,561 ng/mL). Her 59 year-old daughter (who does not have hereditary stomatocytosis) had transferrin saturation 42%, serum ferritin 62 ng/mL, HLA type A1, 32; B14, 15; Bw4, 6; Cw3, 8, and HFE genotype S65C/H63D. These data permitted assignment of the S65C mutation in this family to a haplotype carrying HLA-A32; linkage of S65C and HLA-A32 was also observed in the family of Proband 3.

TABLE 8

Frequencies of HFE Alleles in Alabama Subjects.

| | wt* | C282Y | H63D | S65C† | I105T | G93R |
|---|---|---|---|---|---|---|
| Hemochromatosis Probands with "Atypical" HFE Genotypes (n = 20) | 0.500 | 0.275 | 0.125 | 0.050 | 0.025 | 0.025 |
| Normal Control Subjects (n = 176) | 0.750 | 0.099 | 0.145 | 0.006 | ‡ | ‡ |

The wild-type (wt) allele was defined as an HFE allele in which the mutations C282Y, H63D, S65C, I105T, or G93R were not detected.
†S65C was detected in 2 of 22 (0.091) proband chromosomes and in 2 of 266 (0.0075) control chromosomes that did not bear the C282Y, H63D, S65C, I105T, or G93R mutation.
‡Based on this data set, the frequency of the I105T and G93R HFE alleles is estimated to be < 0.0028, respectively.

intron 4 (nt 6884T→C) was detected in probands 3 and 4, both of whom also had S65C. Subjects that tested positive for the S65C mutation all were found to have the intron 4 (6884T→C) mutation, including two probands (3 and 4), their families, and two normal controls.

EXAMPLE 6

HFE Coding Region Mutations and Clinical Phenotype

Figure 3:
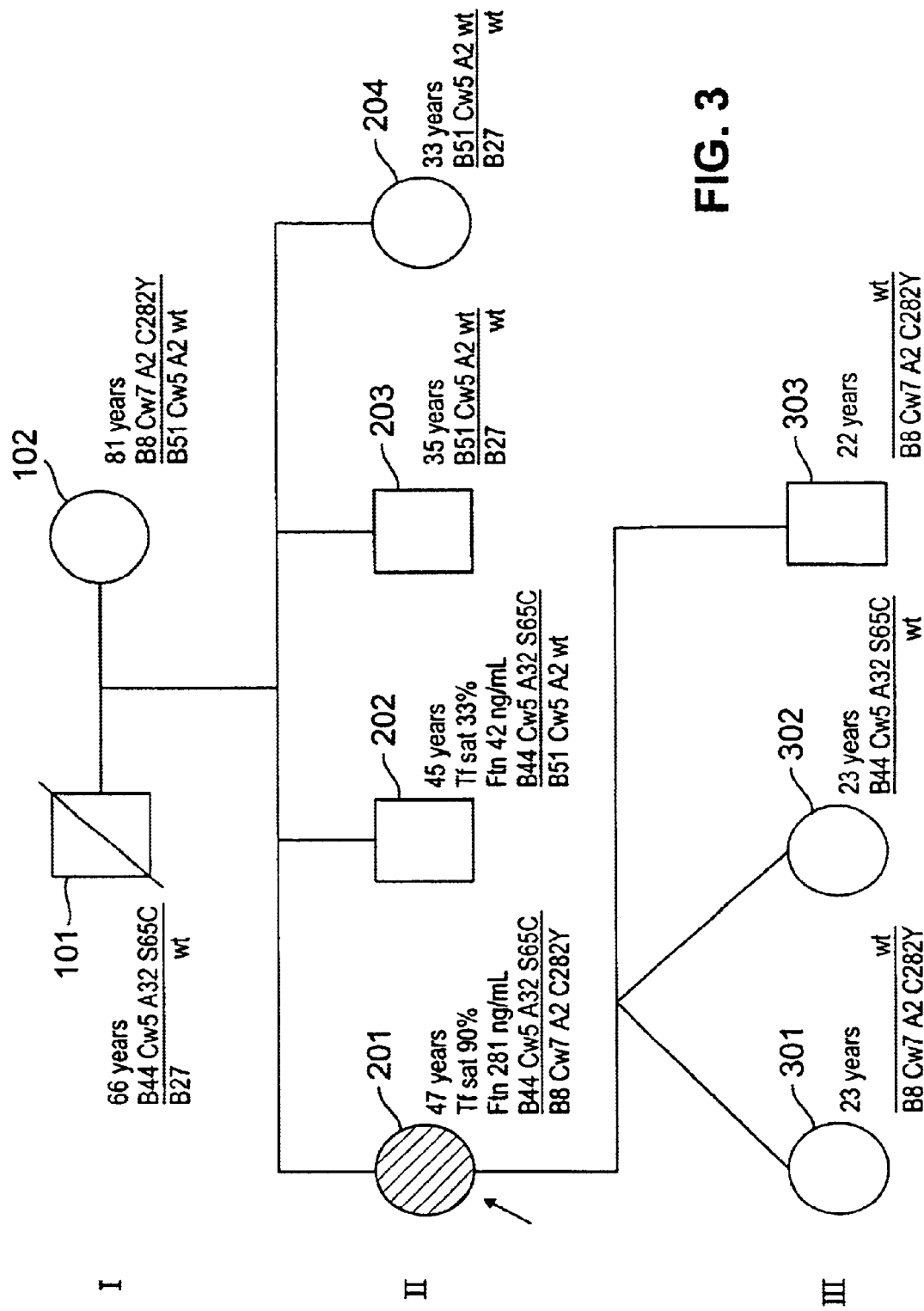
FIG. 3 is a diagram of the family of proband 3 (HFE genotype C282Y/S65C). Symbols and abbreviations are the same as those described for FIG. 1. Proband 3 is indicated with an arrow. S65C, C282Y, and wt alleles are know to exist only on separate chromosomes. Proband 3 also has porphyria cutanea tarda, and her brother (II, 203) has ankylosing spondylitis.

The I105T and G93R mutations were associated with a hemochromatosis clinical phenotype in probands 1 and 2 who also inherited H63D and C282Y, respectively. Proband 3 had clinical evidence of hemochromatosis, iron overload, and porphyria cutanea tarda associated with compound heterozygosity for C282Y and S65C. Proband 4 had severe iron overload associated with heterozygosity for S65C and co-inheritance of hereditary stomatocytosis (Table 7). The sister of proband 1 (HFE genotype I105T/wt) was not completely evaluated for hyperferritinemia (FIG. 1). Otherwise, family members of probands who were heterozygous for novel HFE mutations described herein had little or no evidence of abnormal iron parameters, a hemochromatosis phenotype, or of iron overload (Table 7 and 9; FIGS. 1 and 3). Normal Control 1 who had HFE genotype S65C/wt had a

EXAMPLE 7

HLA Gene Linkage

In the family of proband 1, the I105T mutation was linked to HLA-A3, B7, markers which are often linked to the C282Y mutation and its ancestral haplotype. HLA-A3, B7 is also significantly more common among C282Y-negative hemochromatosis probands than in normal control subjects tested. S65C was linked to HLA-A32 in probands 3 and 4 (and their respective families). The base-pair change in intron 4 (nt 6884T→C) was detected only in probands who inherited the S65C mutation. These data indicate that an intron 4 mutation (nt 6884→C) is a marker for chromosomes bearing the S65C HFE allele. Three of four probands who inherited mutated HFE exon 2 mutations described herein also inherited the C282Y or H63D mutations on separate chromosomes. In a fourth proband, the co-inheritance of S65C heterozygosity and hereditary stomatocytosis was associated with severe iron overload.

Altered interactions of transferrin receptor, transferrin, and C282Y and H63D mutant HFE protein contribute to the pathology of hemochromatosis. The S65C, G93R, and I105T mutations are located within the a1 domain: in the α1 helix of the HFE class I-like heavy chain (I105T and G93R), and at the tip of the A chain loop of the β-pleated sheet

TABLE 9

Hemochromatiosis (HC) Family study/patent

| Subject/Age/Sex | HLA Type | exon 2 | exon 4 | intron 4 5636 bp | Tf sat** % | Ftn** ng/ml | Diagnosis/Hepatocyte Iron grade |
|---|---|---|---|---|---|---|---|
| Proband 1/57M (201) | A2, 3; B7, 7 | H63D/H, I105T/1 | Wt | T | 62 | 868 | HC/2+ |
| brother/45M (204) | | H63D/H | Wt | T* | 31 | 186 | |
| sister/50F (203) | A3, 3; B7, 7 | I105T | Wt* | T* | 37 | 576 | |
| daughter/31F (301) | A32, 68; B7, 44 | I105T/1 | Wt* | T* | 31 | 56 | |
| son/27M (302) | A2, 68; B7, 44 | H63D/H | Wt* | T* | 33 | 44 | |
| Proband 2/40M | A2, 3; B7, 62 | G93R/G | C282Y/C | T | 78 | 861 | HC/4+ |
| Father | | Wt | C282Y/Y* | T* | | | HC |
| Sister | | G93R/G | C282Y/C* | T* | | | HC |
| Proband 3/47 (201) | A2, 32; B8, 44 | S65C/S | C282Y/C | T/C | 90 | 281 | HC/3+ |
| brother/45M (202) | A2, 32; B44, 51 | S65C/S | Wt | T/C | 33 | 42 | |
| mother/81F (102) | A2, 2; B8, 51 | Wt | C282Y/C | T* | NT | NT | |
| sister/33F (204) | A2, 7; B27, 51 | Wt | Wt | T* | NT | NT | |
| brother/35M (203) | A2, 7; B27, 51 | Wt | Wt* | T* | NT | NT | |
| sister | | Wt | C282Y/C* | T* | | | |
| sister | | S65C/S | Wt* | T/C* | | | |
| Proband 4/81F | A2, 32; B14, 62 | S65C/S | Wt | T/C | 100 | S135 | HC + stomatocytosis |
| daughter/59" | A1, 32; B14, 15 | H63D/H, S65C/S | Wt* | T/C | 42 | 62 | |
| Control 1/28M | A2, 31; B35, 60 | S65C/S | Wt | T/C | 28 | 141 | |
| Control 2/69M | A24, 26; B8, 37 | S65C/S | Wt | T/C | 42 | 747 | 2+ |

*RE cut
**normal (15–45%)
***20–300 ng/ml (men)
2C–200 ng/ml (women)

normal iron phenotype (Table 7). Normal Control 2, who also had the HFE genotype S65C/wt, had hyperferritinemia and mildly increased stainable hepatocellular iron deposition, but had no symptoms or other objective findings attributable to iron overload (Table 7). These data indicate that S65C heterozygosity is associated with abnormal iron parameters.

(S65C). These mutations affect the overall structure of the HFE gene product, and specifically affect the salt bridge between residues H63 and D95. The I105T substitution also inhibits proper folding of the α1 domain of the HFE gene product, and specifically affects the hydrophobicity of the hydrophobic F pocket.

Other embodiments are within the following claims.

What is claimed is:

1. A method of diagnosing an iron disorder or a genetic susceptibility to developing said disorder in a mammal, comprising determining the presence of a mutation in exon 2 of a histocompatibility iron loading (HFE) nucleic acid in a biological sample from said mammal, wherein said mutation is at position 193 of SEQ ID NO: 1 and is not a C→G substitution at nucleotide 187 of SEQ ID NO: 1 and wherein the presence of said mutation is indicative of said disorder or a genetic susceptibility to developing said disorder and wherein said determining step is carried out by nucleic acid hybridization on a microchip.

2. The method of claim 1, wherein said disorder is hemochromatosis.

3. The method of claim 1, wherein said mutation at position 193 of SEQ ID NO:1 is an A→T substitution.

4. The method of claim 1, wherein said mutation at position 193 is determined by contacting said HFE nucleic acid with a nucleic acid sequence comprising the nucleotide sequence of SEQ ID NO:30.

5. The method of claim 1, wherein said mutation at position 193 is determined by contacting said HFE nucleic acid with a nucleic acid sequence comprising nucleotides 67–339 of SEQ ID NO:1.

6. The method of claim 1, wherein said mutation at position 193 is determined by contacting said HFE nucleic acid with a nucleic acid sequence comprising nucleotides 172–204 of SEQ ID NO:1.

7. The method of claim 1, wherein said mutation at position 193 is detected by contacting said HFE nucleic acid with a nucleic acid sequence comprising nucleotides 4652–4915 of SEQ ID NO:27.

8. The method of claim 1, further comprising determining the presence of a mutation in exon 4 at nucleotide 845 of SEQ ID NO:1.

9. The method of claim 8, wherein said mutation at position 845 is determined by contacting said HFE nucleic acid with a nucleic acid sequence comprising nucleotides 6494–6769 of SEQ ID NO:27.

10. The method of claim 1, further comprising determining the presence of a mutation in intron 4 at nucleotide 6884 of SEQ ID NO:27.

11. The method of claim 10, wherein said mutation at position 6884 is determined by contacting said HFE nucleic acid with a nucleic acid sequence comprising nucleotides 6770–6927 of SEQ ID NO:27.

* * * * *